(12) United States Patent
Tseng et al.

(10) Patent No.: US 8,076,089 B2
(45) Date of Patent: Dec. 13, 2011

(54) BIOMARKERS FOR LIVER DISEASES AND METHOD FOR USING THE SAME

(75) Inventors: Tzu Ling Tseng, Chiayi (TW); Ping Fu Cheng, Changhua County (TW)

(73) Assignee: Industrial Technology Research Institute, Hsinchu (TW)

( * ) Notice: Subject to any disclaimer, the term of this patent is extended or adjusted under 35 U.S.C. 154(b) by 0 days.

(21) Appl. No.: 12/763,453

(22) Filed: Apr. 20, 2010

(65) Prior Publication Data

US 2010/0261209 A1 Oct. 14, 2010

Related U.S. Application Data

(60) Continuation of application No. 12/073,603, filed on Mar. 7, 2008, now abandoned, which is a division of application No. 11/013,684, filed on Dec. 17, 2004, now abandoned.

(30) Foreign Application Priority Data

Dec. 19, 2003 (TW) ................................ 92136309 A

(51) Int. Cl.
*G01N 33/53* (2006.01)
(52) U.S. Cl. ........................................................ 435/7.1
(58) Field of Classification Search ........................ None
See application file for complete search history.

(56) References Cited

U.S. PATENT DOCUMENTS

| 4,487,830 | A | * | 12/1984 | Coates et al. | ................ | 435/7.23 |
| 6,087,117 | A | | 7/2000 | King et al. | | |
| 6,329,198 | B1 | | 12/2001 | King et al. | | |
| 6,423,836 | B1 | | 7/2002 | King et al. | | |
| 2003/0153013 | A1 | | 8/2003 | Huang | | |

FOREIGN PATENT DOCUMENTS

JP 10319019 4/1998

OTHER PUBLICATIONS

Gonzalez et al. 'Molecular cloning and sequencing of zeta-crystallin/quinone reductase cDNA from human liver.' Biochem. Biophys. Res. Commun. 191:902-907, 1993.*
Tang et al. 'Identification of ζ-Crystallin/NADPH:Quinone Reductase as a Renal Glutaminase mRNA pH Response Element-binding Protein.' J. Biol. Chem. 276(24):21375-211380, 2011.*
Schmits et al., Analysis of the antibody repertoire of astrocytoma patients against antigens expressed by gliomas, Int. J. Cancer, vol. 98, pp. 73-77, 2002.
Lerner et al., Tapping the immunological repertoire to produce antibodies of predetermined specificity, Nature, vol. 299, pp. 592-596, 1982.
Le Naour et al., A distance repertoire of autoantibodies in hepatocellular carcinoma identified by proteomic analysis, Molec & Cellular Proteomics, vol. 1, pp. 197-203, 2002.

\* cited by examiner

*Primary Examiner* — Nora Rooney
(74) *Attorney, Agent, or Firm* — Bacon & Thomas, PLLC

(57) ABSTRACT

Biomarkers for liver diseases and method for using the same are provided. For detecting liver cirrhosis and liver cancer, the biomarkers are selected from any one of the amino acid sequences with SEQ ID NO:1 to SEQ ID NO:24 or derivatives or fragments or variants or the combination thereof or the antibodies against the amino acid sequences. Then the biomarkers are further developed into detection kits, such that by detecting the existence of autoantibodies or autoantigens in screened specimens, liver diseases are detected with higher accuracy and sensitivity.

8 Claims, 2 Drawing Sheets

SEQUENCE LISTING

```
<160> NUMBER OF SEQ ID NOS: 24

<210> SEQ ID NO 1
<211> LENGTH: 151
<212> TYPE: PRT
<213> ORGANISM: Human

<400> SEQUENCE: 1

Ala Asn Leu Glu Arg Thr Phe Ile Ala Ile Lys Pro Asp Gly Val Gln
1               5                   10                  15

Arg Gly Leu Val Gly Glu Ile Ile Lys Arg Phe Glu Gln Lys Gly Phe
            20                  25                  30

Arg Leu Val Ala Met Lys Phe Leu Arg Ala Ser Glu Glu His Leu Lys
        35                  40                  45

Gln His Tyr Ile Asp Leu Lys Asp Arg Pro Phe Phe Pro Gly Leu Val
    50                  55                  60

Lys Tyr Met Asn Ser Gly Pro Val Val Ala Met Val Trp Glu Gly Leu
65                  70                  75                  80

Asn Val Val Lys Thr Gly Arg Val Met Leu Gly Glu Thr Asn Pro Ala
                85                  90                  95

Asp Ser Lys Pro Gly Thr Ile Arg Gly Asp Phe Cys Ile Gln Val Gly
            100                 105                 110

Arg Asn Ile Ile His Gly Ser Asp Ser Val Lys Ser Ala Glu Lys Glu
        115                 120                 125

Ile Ser Leu Trp Phe Lys Pro Glu Glu Leu Val Asp Tyr Lys Ser Cys
    130                 135                 140

Ala His Asp Trp Val Tyr Glu
145                 150

<210> SEQ ID NO 2
<211> LENGTH: 180
```

```
<212> TYPE: PRT
<213> ORGANISM: Human

<400> SEQUENCE: 2

Cys Cys Glu Pro Arg Gly Ser Arg Ala Arg Phe Gly Cys Trp Arg Leu
1               5                   10                  15

Gln Pro Glu Phe Lys Pro Lys Gln Leu Glu Gly Thr Met Ala Asn Cys
            20                  25                  30

Glu Arg Thr Phe Ile Ala Ile Lys Pro Asp Gly Val Gln Arg Gly Leu
        35                  40                  45

Val Gly Glu Ile Ile Lys Arg Phe Glu Gln Lys Gly Phe Arg Leu Val
50                  55                  60

Gly Leu Lys Phe Met Gln Ala Ser Glu Asp Leu Leu Lys Glu His Tyr
65                  70                  75                  80

Val Asp Leu Lys Asp Arg Pro Phe Phe Ala Gly Leu Val Lys Tyr Met
                85                  90                  95

His Ser Gly Pro Val Val Ala Met Val Trp Glu Gly Leu Asn Val Val
            100                 105                 110

Lys Thr Gly Arg Val Met Leu Gly Glu Thr Asn Pro Ala Asp Ser Lys
        115                 120                 125

Pro Gly Thr Ile Arg Gly Asp Phe Cys Ile Gln Val Gly Arg Asn Ile
130                 135                 140

Ile His Gly Ser Asp Ser Val Glu Ser Ala Glu Lys Glu Ile Gly Leu
145                 150                 155                 160

Trp Phe His Pro Glu Glu Leu Val Asp Tyr Thr Ser Cys Ala Gln Asn
                165                 170                 175

Trp Ile Tyr Glu
            180

<210> SEQ ID NO 3
<211> LENGTH: 539
<212> TYPE: PRT
<213> ORGANISM: Human

<400> SEQUENCE: 3

Met Thr Ser Leu Trp Gly Lys Gly Thr Gly Cys Lys Leu Phe Lys Phe
1               5                   10                  15

Arg Val Ala Ala Ala Pro Ala Ser Gly Ala Leu Arg Arg Leu Thr Pro
            20                  25                  30

Ser Ala Ser Leu Pro Pro Ala Gln Leu Leu Leu Arg Ala Val Arg Arg
        35                  40                  45

Arg Ser His Pro Val Arg Asp Tyr Ala Ala Gln Thr Ser Pro Ser Pro
50                  55                  60

Lys Ala Gly Ala Ala Thr Gly Arg Ile Val Ala Val Ile Gly Ala Val
65                  70                  75                  80

Val Asp Val Gln Phe Asp Glu Gly Leu Pro Pro Ile Leu Asn Ala Leu
                85                  90                  95

Glu Val Gln Gly Arg Glu Thr Arg Leu Val Leu Glu Val Ala Gln His
            100                 105                 110

Leu Gly Glu Ser Thr Val Arg Thr Ile Ala Met Asp Gly Thr Glu Gly
        115                 120                 125

Leu Val Arg Gly Gln Lys Val Leu Asp Ser Gly Ala Pro Ile Lys Ile
130                 135                 140

Pro Val Gly Pro Glu Thr Leu Gly Arg Ile Met Asn Val Ile Gly Glu
145                 150                 155                 160

Pro Ile Asp Glu Arg Gly Pro Ile Lys Thr Lys Gln Phe Ala Pro Ile
```

```
                   165                 170                 175
His Ala Glu Ala Pro Glu Phe Met Glu Met Ser Val Glu Gln Glu Ile
            180                 185                 190

Leu Val Thr Gly Ile Lys Val Val Asp Leu Leu Ala Pro Tyr Ala Lys
        195                 200                 205

Gly Gly Lys Ile Gly Leu Phe Gly Gly Ala Gly Val Gly Lys Thr Val
    210                 215                 220

Leu Ile Met Glu Leu Ile Asn Asn Val Ala Lys Ala His Gly Gly Tyr
225                 230                 235                 240

Ser Val Phe Ala Gly Val Gly Glu Arg Thr Arg Glu Gly Asn Asp Leu
                245                 250                 255

Tyr His Glu Met Ile Glu Ser Gly Val Ile Asn Leu Lys Asp Ala Thr
            260                 265                 270

Ser Lys Val Ala Leu Val Tyr Gly Gln Met Asn Glu Pro Pro Gly Ala
        275                 280                 285

Arg Ala Arg Val Ala Leu Thr Gly Leu Thr Val Ala Glu Tyr Phe Arg
    290                 295                 300

Asp Gln Glu Gly Gln Asp Val Leu Leu Phe Ile Asp Asn Ile Phe Arg
305                 310                 315                 320

Phe Thr Gln Ala Gly Ser Glu Val Ser Ala Leu Leu Gly Arg Ile Pro
                325                 330                 335

Ser Ala Val Gly Tyr Gln Pro Thr Leu Ala Thr Asp Met Gly Thr Met
            340                 345                 350

Gln Glu Arg Ile Thr Thr Thr Lys Lys Gly Ser Ile Thr Ser Val Gln
        355                 360                 365

Ala Ile Tyr Val Pro Ala Asp Asp Leu Thr Asp Pro Ala Pro Ala Thr
    370                 375                 380

Thr Phe Ala His Leu Asp Ala Thr Thr Val Leu Ser Arg Ala Ile Ala
385                 390                 395                 400

Glu Leu Gly Ile Tyr Pro Ala Val Asp Pro Leu Asp Ser Thr Ser Arg
                405                 410                 415

Ile Met Asp Pro Asn Ile Val Gly Ser Glu His Tyr Asp Val Ala Arg
            420                 425                 430

Gly Val Gln Lys Ile Leu Gln Asp Tyr Lys Ser Leu Gln Asp Ile Ile
        435                 440                 445

Ala Ile Leu Gly Met Asp Glu Leu Ser Glu Glu Asp Lys Leu Thr Val
    450                 455                 460

Ser Arg Ala Arg Lys Ile Gln Arg Phe Leu Ser Gln Pro Phe Gln Val
465                 470                 475                 480

Ala Glu Val Phe Thr Gly His Met Gly Lys Leu Val Pro Leu Lys Glu
                485                 490                 495

Thr Ile Lys Gly Phe Gln Gln Ile Leu Ala Gly Glu Tyr Asp His Leu
            500                 505                 510

Pro Glu Gln Ala Phe Tyr Met Val Gly Pro Ile Glu Glu Ala Val Ala
        515                 520                 525

Lys Ala Asp Lys Leu Ala Glu Glu His Ser Ser
    530                 535

<210> SEQ ID NO 4
<211> LENGTH: 245
<212> TYPE: PRT
<213> ORGANISM: Human

<400> SEQUENCE: 4

Met Asp Lys Asn Glu Leu Val Gln Lys Ala Lys Leu Ala Glu Gln Ala
```

```
            1               5                  10                 15
Glu Arg Tyr Asp Asp Met Ala Ala Cys Met Lys Ser Val Thr Glu Gln
                20                 25                 30

Gly Ala Glu Leu Ser Asn Glu Arg Asn Leu Leu Ser Val Ala Tyr
            35                 40                 45

Lys Asn Val Val Gly Ala Arg Arg Ser Ser Trp Arg Val Val Ser Ser
        50                 55                 60

Ile Glu Gln Lys Thr Glu Gly Ala Glu Lys Lys Gln Gln Met Ala Arg
65                 70                 75                 80

Glu Tyr Arg Glu Lys Ile Glu Thr Glu Leu Arg Asp Ile Cys Asn Asp
                85                 90                 95

Val Leu Ser Leu Leu Glu Lys Phe Leu Ile Pro Asn Ala Ser Gln Ala
            100                105                110

Glu Ser Lys Val Phe Tyr Leu Lys Met Lys Gly Asp Tyr Tyr Arg Tyr
            115                120                125

Leu Ala Glu Val Ala Ala Gly Asp Asp Lys Lys Gly Ile Val Asp Gln
            130                135                140

Ser Gln Gln Ala Tyr Gln Glu Ala Phe Glu Ile Ser Lys Lys Glu Met
145                150                155                160

Gln Pro Thr His Pro Ile Arg Leu Gly Leu Ala Leu Asn Phe Ser Val
                165                170                175

Phe Tyr Tyr Glu Ile Leu Asn Ser Pro Glu Lys Ala Cys Ser Leu Ala
                180                185                190

Lys Thr Ala Phe Asp Glu Ala Ile Ala Glu Leu Asp Thr Leu Ser Glu
            195                200                205

Glu Ser Tyr Lys Asp Ser Thr Leu Ile Met Gln Leu Leu Arg Asp Asn
            210                215                220

Leu Thr Leu Trp Thr Ser Asp Thr Gln Gly Asp Glu Ala Glu Ala Gly
225                230                235                240

Glu Gly Gly Glu Asn
            245

<210> SEQ ID NO 5
<211> LENGTH: 255
<212> TYPE: PRT
<213> ORGANISM: Human

<400> SEQUENCE: 5

Met Asp Asp Arg Glu Asp Leu Val Tyr Gln Ala Lys Leu Ala Glu Gln
1               5                  10                 15

Ala Glu Arg Tyr Asp Glu Met Val Glu Ser Met Lys Lys Val Ala Gly
                20                 25                 30

Met Asp Val Glu Leu Thr Val Glu Glu Arg Asn Leu Leu Ser Val Ala
            35                 40                 45

Tyr Lys Asn Val Ile Gly Ala Arg Arg Ala Ser Trp Arg Ile Ile Ser
        50                 55                 60

Ser Ile Glu Gln Lys Glu Glu Asn Lys Gly Gly Glu Asp Lys Leu Lys
65                 70                 75                 80

Met Ile Arg Glu Tyr Arg Gln Met Val Glu Thr Glu Leu Lys Leu Ile
                85                 90                 95

Cys Cys Asp Ile Leu Asp Val Leu Asp Lys His Leu Ile Pro Ala Ala
            100                105                110

Asn Thr Gly Glu Ser Lys Val Phe Tyr Tyr Lys Met Lys Gly Asp Tyr
            115                120                125

His Arg Tyr Leu Ala Glu Phe Ala Thr Gly Asn Asp Arg Lys Glu Ala
```

```
                130                 135                 140
Ala Glu Asn Ser Leu Val Ala Tyr Lys Ala Ala Ser Asp Ile Ala Met
145                 150                 155                 160

Thr Glu Leu Pro Pro Thr His Pro Ile Arg Leu Gly Leu Ala Leu Asn
                165                 170                 175

Phe Ser Val Phe Tyr Tyr Glu Ile Leu Asn Ser Pro Asp Arg Ala Cys
                180                 185                 190

Arg Leu Ala Lys Ala Ala Phe Asp Asp Ala Ile Ala Glu Leu Asp Thr
                195                 200                 205

Leu Ser Glu Glu Ser Tyr Lys Asp Ser Thr Leu Ile Met Gln Leu Leu
                210                 215                 220

Arg Asp Asn Leu Thr Leu Trp Thr Ser Asp Met Gln Gly Asp Gly Glu
225                 230                 235                 240

Glu Gln Asn Lys Glu Ala Leu Gln Asp Val Glu Asp Glu Asn Gln
                245                 250                 255

<210> SEQ ID NO 6
<211> LENGTH: 421
<212> TYPE: PRT
<213> ORGANISM: Human

<400> SEQUENCE: 6

Leu Tyr Ser Ser Asp Asp Val Ile Glu Leu Thr Pro Ser Asn Phe
1                 5                  10                  15

Asn Arg Glu Val Ile Gln Ser Asp Ser Leu Trp Leu Val Glu Phe Tyr
                20                  25                  30

Ala Pro Trp Cys Gly His Cys Gln Arg Leu Thr Pro Glu Trp Lys Lys
                35                  40                  45

Ala Ala Thr Ala Leu Lys Asp Val Val Lys Val Gly Ala Val Asp Ala
                50                  55                  60

Asp Lys His His Ser Leu Gly Gly Gln Tyr Gly Val Gln Gly Phe Pro
65                  70                  75                  80

Thr Ile Lys Ile Phe Gly Ser Asn Lys Asn Arg Pro Glu Asp Tyr Gln
                85                  90                  95

Gly Gly Arg Thr Gly Glu Ala Ile Val Asp Ala Ala Leu Ser Ala Leu
                100                 105                 110

Arg Gln Leu Val Lys Asp Arg Leu Gly Gly Arg Ser Gly Gly Tyr Ser
                115                 120                 125

Ser Gly Lys Gln Gly Arg Ser Asp Ser Ser Lys Lys Asp Val Ile
                130                 135                 140

Glu Leu Thr Asp Asp Ser Phe Asp Lys Asn Val Leu Asp Ser Glu Asp
145                 150                 155                 160

Val Trp Met Val Glu Phe Tyr Ala Pro Trp Cys Gly His Cys Lys Asn
                165                 170                 175

Leu Glu Pro Glu Trp Ala Ala Ala Ala Ser Glu Val Lys Glu Gln Thr
                180                 185                 190

Lys Gly Arg Val Lys Leu Ala Ala Val Asp Ala Thr Val Asn Gln Val
                195                 200                 205

Leu Ala Ser Arg Tyr Gly Ile Arg Gly Phe Pro Thr Ile Lys Ile Phe
                210                 215                 220

Gln Lys Gly Glu Ser Pro Val Asp Tyr Asp Gly Gly Arg Thr Arg Ser
225                 230                 235                 240

Asp Ile Val Ser Arg Ala Leu Asp Leu Phe Ser Asp Asn Ala Pro Pro
                245                 250                 255

Pro Glu Leu Leu Glu Ile Ile Asn Glu Asp Ile Ala Lys Arg Thr Cys
```

```
                260                 265                 270
Glu Glu His Gln Leu Cys Val Val Ala Val Leu Pro His Ile Leu Asp
            275                 280                 285
Thr Gly Ala Ala Gly Arg Asn Ser Tyr Leu Glu Val Leu Leu Lys Leu
        290                 295                 300
Ala Asp Lys Tyr Lys Lys Met Trp Gly Trp Leu Trp Thr Glu Ala
305                 310                 315                 320
Gly Ala Gln Ser Glu Leu Glu Thr Ala Leu Gly Ile Gly Gly Phe Gly
                325                 330                 335
Tyr Pro Ala Met Ala Ala Ile Asn Ala Arg Lys Met Lys Phe Ala Leu
            340                 345                 350
Leu Lys Gly Ser Phe Ser Glu Gln Gly Ile Asn Glu Phe Leu Arg Glu
        355                 360                 365
Leu Ser Phe Gly Arg Gly Ser Thr Ala Pro Val Gly Gly Ala Phe
370                 375                 380
Pro Thr Ile Val Glu Arg Glu Pro Trp Asp Gly Arg Asp Gly Glu Leu
385                 390                 395                 400
Pro Val Glu Asp Asp Ile Asp Leu Ser Asp Val Glu Leu Asp Asp Leu
                405                 410                 415
Gly Lys Asp Glu Leu
            420

<210> SEQ ID NO 7
<211> LENGTH: 687
<212> TYPE: PRT
<213> ORGANISM: Human

<400> SEQUENCE: 7

Met Val Lys Leu Ala Lys Ala Gly Lys Asn Gln Gly Asp Pro Lys Lys
1               5                   10                  15
Met Ala Pro Pro Lys Glu Val Glu Glu Asp Ser Glu Asp Glu Glu
            20                  25                  30
Met Ser Glu Asp Glu Glu Asp Ser Ser Gly Glu Glu Val Val Ile
        35                  40                  45
Pro Gln Lys Lys Gly Lys Lys Ala Ala Ala Thr Ser Ala Lys Lys Val
    50                  55                  60
Val Val Ser Pro Thr Lys Lys Val Ala Val Ala Thr Pro Ala Lys Ala
65                  70                  75                  80
Val Thr Thr Pro Gly Lys Lys Gly Ala Thr Pro Gly Lys Ala Leu Val
                85                  90                  95
Ala Thr Pro Gly Lys Lys Gly Ala Ile Pro Ala Lys Gly Ala Lys
            100                 105                 110
Asn Gly Lys Asn Ala Lys Lys Glu Asp Ser Asp Glu Glu Asp Asp
        115                 120                 125
Asp Ser Glu Glu Asp Glu Glu Asp Asp Glu Asp Glu Asp Glu Asp Glu
    130                 135                 140
Asp Glu Ile Glu Pro Ala Ala Met Lys Ala Ala Ala Ala Pro Ala
145                 150                 155                 160
Ser Glu Asp Glu Asp Asp Glu Asp Asp Glu Asp Asp Glu Asp Asp
                165                 170                 175
Asp Asp Glu Glu Asp Asp Ser Glu Glu Glu Ala Met Glu Thr Thr Pro
            180                 185                 190
Ala Lys Gly Lys Lys Ala Ala Lys Val Val Pro Val Lys Ala Lys Asn
        195                 200                 205
Val Ala Glu Asp Glu Asp Glu Glu Glu Asp Asp Glu Asp Glu Asp Asp
```

```
                210                 215                 220
Asp Asp Asp Glu Asp Asp Glu Asp Asp Asp Glu Asp Asp Glu Glu
225                 230                 235                 240

Glu Glu Glu Glu Glu Glu Glu Glu Pro Val Lys Glu Ala Pro Gly Lys
                245                 250                 255

Arg Lys Lys Glu Met Ala Lys Gln Lys Ala Ala Pro Glu Ala Lys Lys
                260                 265                 270

Gln Lys Val Glu Gly Thr Glu Pro Thr Thr Ala Phe Asn Leu Phe Val
                275                 280                 285

Gly Asn Leu Asn Phe Asn Lys Ser Ala Pro Glu Leu Lys Thr Gly Ile
290                 295                 300

Ser Asp Val Phe Ala Lys Asn Asp Leu Ala Val Val Asp Val Arg Ile
305                 310                 315                 320

Gly Met Thr Arg Lys Phe Gly Tyr Val Asp Phe Glu Ser Ala Glu Asp
                325                 330                 335

Leu Glu Lys Ala Leu Glu Leu Thr Gly Leu Lys Val Phe Gly Asn Glu
                340                 345                 350

Ile Lys Leu Glu Lys Pro Lys Gly Lys Asp Ser Lys Lys Glu Arg Asp
                355                 360                 365

Ala Arg Thr Leu Leu Ala Lys Asn Leu Pro Tyr Lys Val Thr Gln Asp
370                 375                 380

Glu Leu Lys Glu Val Phe Glu Asp Ala Ala Glu Ile Arg Leu Val Ser
385                 390                 395                 400

Lys Asp Gly Lys Ser Lys Gly Ile Ala Tyr Ile Glu Phe Lys Thr Glu
                405                 410                 415

Ala Asp Ala Glu Lys Thr Phe Glu Glu Lys Gln Gly Thr Glu Ile Asp
                420                 425                 430

Gly Arg Ser Ile Ser Leu Tyr Tyr Thr Gly Glu Lys Gly Gln Asn Gln
                435                 440                 445

Asp Tyr Arg Gly Gly Lys Asn Ser Thr Trp Ser Gly Glu Ser Lys Thr
                450                 455                 460

Leu Val Leu Ser Asn Leu Ser Tyr Ser Ala Thr Glu Glu Thr Leu Gln
465                 470                 475                 480

Glu Val Phe Glu Lys Ala Thr Phe Ile Lys Val Pro Gln Asn Gln Asn
                485                 490                 495

Gly Lys Ser Lys Gly Tyr Ala Phe Ile Glu Phe Ala Ser Phe Glu Asp
                500                 505                 510

Ala Lys Glu Ala Leu Asn Ser Cys Asn Lys Arg Glu Ile Gly Gly Arg
                515                 520                 525

Ala Ile Arg Leu Glu Leu Gln Gly Pro Arg Gly Ser Pro Asn Ala Arg
530                 535                 540

Ser Gln Pro Ser Lys Thr Leu Phe Val Lys Gly Leu Ser Glu Asp Thr
545                 550                 555                 560

Thr Glu Glu Thr Leu Lys Glu Ser Phe Asp Gly Ser Val Arg Ala Arg
                565                 570                 575

Ile Val Thr Asp Arg Glu Thr Gly Ser Ser Lys Gly Phe Gly Phe Val
                580                 585                 590

Asp Phe Asn Ser Glu Glu Asp Ala Lys Ala Ala Lys Glu Ala Met Glu
                595                 600                 605

Asp Gly Glu Ile Asp Gly Asn Lys Val Thr Leu Asp Trp Ala Lys Pro
                610                 615                 620

Lys Gly Glu Gly Gly Phe Gly Gly Arg Gly Gly Arg Gly Gly Phe
625                 630                 635                 640
```

```
Gly Gly Arg Gly Gly Arg Gly Gly Arg Gly Gly Phe Gly Gly Arg
                    645                 650                 655

Gly Arg Gly Gly Phe Gly Gly Arg Gly Gly Phe Arg Gly Arg Gly
            660                 665                 670

Gly Gly Gly Asp His Lys Pro Gln Gly Lys Lys Thr Lys Phe Glu
            675                 680                 685

<210> SEQ ID NO 8
<211> LENGTH: 641
<212> TYPE: PRT
<213> ORGANISM: Human

<400> SEQUENCE: 8

Met Ala Gly Ile Thr Thr Ile Glu Ala Val Lys Arg Lys Ile Gln Val
1               5                   10                  15

Leu Gln Gln Gln Ala Asp Asp Ala Glu Glu Arg Ala Glu Arg Leu Gln
                20                  25                  30

Arg Glu Val Glu Gly Glu Arg Arg Ala Arg Glu Gln Ala Glu Ala
            35                  40                  45

Val Ala Ser Leu Asn Arg Arg Ile Gln Leu Val Glu Glu Glu Leu Asp
50                  55                  60

Arg Ala Gln Glu Arg Leu Ala Thr Ala Leu Gln Lys Leu Glu Glu Ala
65                  70                  75                  80

Glu Lys Ala Ala Asp Glu Ser Glu Arg Gly Met Lys Val Ile Glu Asn
                85                  90                  95

Arg Ala Leu Lys Asp Glu Glu Lys Met Glu Leu Gln Glu Ile Gln Leu
            100                 105                 110

Glu Glu Ala Lys His Ile Ala Glu Ala Asp Arg Lys Tyr Glu Glu
            115                 120                 125

Val Ala Arg Lys Leu Val Ile Ile Glu Gly Asp Leu Glu Arg Thr Glu
130                 135                 140

Glu Arg Ala Glu Leu Ala Glu Ser Arg Cys Arg Glu Met Asp Glu Gln
145                 150                 155                 160

Ile Arg Leu Met Asp Gln Asn Leu Lys Cys Leu Ser Ala Ala Glu Glu
                165                 170                 175

Lys Tyr Ser Gln Lys Glu Asp Lys Tyr Glu Glu Ile Lys Ile Leu
            180                 185                 190

Thr Asp Lys Leu Lys Glu Ala Glu Thr Arg Ala Glu Phe Ala Glu Arg
            195                 200                 205

Ser Val Ala Lys Leu Glu Lys Thr Ile Asp Asp Leu Glu Asp Thr Asn
210                 215                 220

Ser Thr Ser Gly Asp Pro Val Glu Lys Lys Asp Glu Thr Pro Phe Gly
225                 230                 235                 240

Val Ser Val Ala Val Gly Leu Ala Val Phe Ala Cys Leu Phe Leu Ser
                245                 250                 255

Thr Leu Leu Val Leu Asn Lys Cys Gly Arg Arg Asn Lys Phe Gly
            260                 265                 270

Ile Asn Arg Pro Ala Val Leu Ala Pro Glu Asp Gly Leu Ala Met Ser
            275                 280                 285

Leu His Phe Met Thr Leu Gly Gly Ser Ser Leu Ser Pro Thr Glu Gly
290                 295                 300

Lys Gly Ser Gly Leu Gln Gly His Ile Ile Glu Asn Pro Gln Tyr Phe
305                 310                 315                 320

Ser Asp Ala Cys Val His His Ile Lys Arg Arg Asp Ile Val Leu Lys
                325                 330                 335
```

```
Trp Glu Leu Gly Glu Gly Ala Phe Gly Lys Val Phe Leu Ala Glu Cys
            340                 345                 350

His Asn Leu Leu Pro Glu Gln Asp Lys Met Leu Val Ala Val Lys Ala
        355                 360                 365

Leu Lys Glu Ala Ser Glu Ser Ala Arg Gln Asp Phe Gln Arg Glu Ala
    370                 375                 380

Glu Leu Leu Thr Met Leu Gln His Gln His Ile Val Arg Phe Phe Gly
385                 390                 395                 400

Val Cys Thr Glu Gly Arg Pro Leu Leu Met Val Phe Glu Tyr Met Arg
                405                 410                 415

His Gly Asp Leu Asn Arg Phe Leu Arg Ser His Gly Pro Asp Ala Lys
            420                 425                 430

Leu Leu Ala Gly Gly Glu Asp Val Ala Pro Gly Pro Leu Gly Leu Gly
        435                 440                 445

Gln Leu Leu Ala Val Ala Ser Gln Val Ala Ala Gly Met Val Tyr Leu
    450                 455                 460

Ala Gly Leu His Phe Val His Arg Asp Leu Ala Thr Arg Asn Cys Leu
465                 470                 475                 480

Val Gly Gln Gly Leu Val Val Lys Ile Gly Asp Phe Gly Met Ser Arg
                485                 490                 495

Asp Ile Tyr Ser Thr Asp Tyr Tyr Arg Val Gly Gly Arg Thr Met Leu
            500                 505                 510

Pro Ile Arg Trp Met Pro Pro Glu Ser Ile Leu Tyr Arg Lys Phe Thr
        515                 520                 525

Thr Glu Ser Asp Val Trp Ser Phe Gly Val Val Leu Trp Glu Ile Phe
    530                 535                 540

Thr Tyr Gly Lys Gln Pro Trp Tyr Gln Leu Ser Asn Thr Glu Ala Ile
545                 550                 555                 560

Asp Cys Ile Thr Gln Gly Arg Glu Leu Glu Arg Pro Arg Ala Cys Pro
                565                 570                 575

Pro Glu Val Tyr Ala Ile Met Arg Gly Cys Trp Gln Arg Glu Pro Ser
            580                 585                 590

Asn Ala Thr Ala Ser Arg Met Cys Thr Pro Gly Cys Lys Pro Trp Pro
        595                 600                 605

Arg His Leu Leu Ser Thr Trp Met Ser Trp Ala Arg Gly Pro Ala Gln
    610                 615                 620

Gly Leu Gly Val Val Ser Arg Asn Thr Gly Ala Cys Pro Gln His Pro
625                 630                 635                 640

Pro

<210> SEQ ID NO 9
<211> LENGTH: 284
<212> TYPE: PRT
<213> ORGANISM: Human

<400> SEQUENCE: 9

Met Glu Ala Ile Lys Lys Met Gln Met Leu Lys Leu Asp Lys Glu
1               5                   10                  15

Asn Ala Ile Asp Arg Ala Glu Gln Ala Glu Ala Asp Lys Lys Ala Ala
            20                  25                  30

Glu Asp Lys Cys Lys Gln Val Glu Glu Leu Thr His Leu Gln Lys
        35                  40                  45

Lys Leu Lys Gly Thr Glu Asp Glu Leu Asp Lys Tyr Ser Glu Asp Leu
    50                  55                  60

Lys Asp Ala Gln Glu Lys Leu Glu Leu Thr Glu Lys Lys Ala Ser Asp
```

```
                65                  70                  75                  80
Ala Glu Gly Asp Val Ala Leu Asn Arg Arg Ile Gln Leu Val Glu
                    85                  90                  95
Glu Glu Leu Asp Arg Ala Gln Glu Arg Leu Ala Thr Ala Leu Gln Lys
                    100                 105                 110
Leu Glu Glu Ala Glu Lys Ala Ala Asp Glu Ser Glu Arg Gly Met Lys
                    115                 120                 125
Val Ile Glu Asn Arg Ala Met Lys Asp Glu Glu Lys Met Glu Ile Gln
                    130                 135                 140
Glu Met Gln Leu Lys Glu Ala Lys His Ile Ala Glu Glu Ala Asp Arg
145                 150                 155                 160
Lys Tyr Glu Glu Val Ala Arg Lys Leu Val Ile Leu Glu Gly Glu Leu
                    165                 170                 175
Glu Arg Ala Glu Glu Arg Ala Glu Val Ser Glu Leu Lys Cys Gly Asp
                    180                 185                 190
Leu Glu Glu Glu Leu Lys Asn Val Thr Asn Asn Leu Lys Ser Leu Glu
                    195                 200                 205
Ala Ala Ser Glu Lys Tyr Ser Glu Lys Glu Asp Lys Tyr Glu Glu Glu
                    210                 215                 220
Ile Lys Leu Leu Ser Asp Lys Leu Lys Glu Ala Glu Thr Arg Ala Glu
225                 230                 235                 240
Phe Ala Glu Arg Thr Val Ala Lys Leu Glu Lys Thr Ile Asp Asp Leu
                    245                 250                 255
Glu Glu Lys Leu Ala Gln Ala Lys Glu Glu Asn Val Gly Leu His Gln
                    260                 265                 270
Thr Leu Asp Gln Thr Leu Asn Glu Leu Asn Cys Ile
                    275                 280

<210> SEQ ID NO 10
<211> LENGTH: 417
<212> TYPE: PRT
<213> ORGANISM: Human

<400> SEQUENCE: 10

Met Leu Leu Ser Val Pro Leu Leu Gly Leu Leu Gly Leu Ala Val
1               5                   10                  15
Ala Glu Pro Ala Val Tyr Phe Lys Glu Gln Phe Leu Asp Gly Asp Gly
                    20                  25                  30
Trp Thr Ser Arg Trp Ile Glu Ser Lys His Lys Ser Asp Phe Gly Lys
                    35                  40                  45
Phe Val Leu Ser Ser Gly Lys Phe Tyr Gly Asp Glu Glu Lys Asp Lys
                    50                  55                  60
Gly Leu Gln Thr Ser Gln Asp Ala Arg Phe Tyr Ala Leu Ser Ala Ser
65                  70                  75                  80
Phe Glu Pro Phe Ser Asn Lys Gly Gln Thr Leu Val Val Gln Phe Thr
                    85                  90                  95
Val Lys His Glu Gln Asn Ile Asp Cys Gly Gly Gly Tyr Val Lys Leu
                    100                 105                 110
Phe Pro Asn Ser Leu Asp Gln Thr Asp Met His Gly Asp Ser Glu Tyr
                    115                 120                 125
Asn Ile Met Phe Gly Pro Asp Ile Cys Gly Pro Gly Thr Lys Lys Val
                    130                 135                 140
His Val Ile Phe Asn Tyr Lys Gly Lys Asn Val Leu Ile Asn Lys Asp
145                 150                 155                 160
Ile Arg Cys Lys Asp Asp Glu Phe Thr His Leu Tyr Thr Leu Ile Val
```

```
                          165                 170                 175
Arg Pro Asp Asn Thr Tyr Glu Val Lys Ile Asp Asn Ser Gln Val Glu
                180                 185                 190

Ser Gly Ser Leu Glu Asp Asp Trp Asp Phe Leu Pro Pro Lys Lys Ile
            195                 200                 205

Lys Asp Pro Asp Ala Ser Lys Pro Glu Asp Trp Asp Glu Arg Ala Lys
        210                 215                 220

Ile Asp Asp Pro Thr Asp Ser Lys Pro Glu Asp Trp Asp Lys Pro Glu
225                 230                 235                 240

His Ile Pro Asp Pro Asp Ala Lys Lys Pro Glu Asp Trp Asp Glu Glu
                245                 250                 255

Met Asp Gly Glu Trp Glu Pro Pro Val Ile Gln Asn Pro Glu Tyr Lys
            260                 265                 270

Gly Glu Trp Lys Pro Arg Gln Ile Asp Asn Pro Asp Tyr Lys Gly Thr
        275                 280                 285

Trp Ile His Pro Glu Ile Asp Asn Pro Glu Tyr Ser Pro Asp Pro Ser
290                 295                 300

Ile Tyr Ala Tyr Asp Asn Phe Gly Val Leu Gly Leu Asp Leu Trp Gln
305                 310                 315                 320

Val Lys Ser Gly Thr Ile Phe Asp Asn Phe Leu Ile Thr Asn Asp Glu
                325                 330                 335

Ala Tyr Ala Glu Glu Phe Gly Asn Glu Thr Trp Gly Val Thr Lys Ala
            340                 345                 350

Ala Glu Lys Gln Met Lys Asp Lys Gln Asp Glu Glu Gln Arg Leu Lys
        355                 360                 365

Glu Glu Glu Glu Asp Lys Lys Arg Lys Glu Glu Glu Ala Glu Asp
370                 375                 380

Lys Glu Asp Asp Glu Asp Lys Asp Glu Asp Glu Asp Glu Glu Asp
385                 390                 395                 400

Lys Glu Glu Asp Glu Glu Glu Asp Val Pro Gly Gln Ala Lys Asp Glu
                405                 410                 415

Leu

<210> SEQ ID NO 11
<211> LENGTH: 278
<212> TYPE: PRT
<213> ORGANISM: Human

<400> SEQUENCE: 11

Leu Arg Cys Val Pro Arg Val Leu Gly Ser Ser Val Ala Gly Leu Arg
1               5                   10                  15

Ala Ala Ala Pro Ala Ser Pro Phe Arg Gln Leu Leu Gln Pro Ala Pro
            20                  25                  30

Arg Leu Cys Thr Arg Pro Phe Gly Leu Leu Ser Val Arg Ala Gly Ser
        35                  40                  45

Glu Arg Arg Pro Gly Leu Leu Arg Pro Arg Gly Pro Cys Ala Cys Gly
    50                  55                  60

Cys Gly Cys Gly Ser Leu His Thr Asp Gly Asp Lys Ala Phe Val Asp
65                  70                  75                  80

Phe Leu Ser Asp Glu Ile Lys Glu Glu Arg Lys Ile Gln Lys His Lys
                85                  90                  95

Thr Leu Pro Lys Met Ser Gly Gly Trp Glu Leu Glu Leu Asn Gly Thr
            100                 105                 110

Glu Ala Lys Leu Val Arg Lys Val Ala Gly Glu Lys Ile Thr Val Thr
        115                 120                 125
```

```
Phe Asn Ile Asn Asn Ser Ile Pro Pro Thr Phe Asp Gly Glu Glu Glu
    130                 135                 140

Pro Ser Gln Gly Gln Lys Val Glu Glu Gln Glu Pro Glu Leu Thr Ser
145                 150                 155                 160

Thr Pro Asn Phe Val Val Glu Val Ile Lys Asn Asp Asp Gly Lys Lys
                165                 170                 175

Ala Leu Val Leu Asp Cys His Tyr Pro Glu Asp Glu Val Gly Gln Glu
            180                 185                 190

Asp Glu Ala Glu Ser Asp Ile Phe Ser Ile Arg Glu Val Ser Phe Gln
        195                 200                 205

Ser Thr Gly Glu Ser Glu Trp Lys Asp Thr Asn Tyr Thr Leu Asn Thr
    210                 215                 220

Asp Ser Leu Asp Trp Ala Leu Tyr Asp His Leu Met Asp Phe Leu Ala
225                 230                 235                 240

Asp Arg Gly Val Asp Asn Thr Phe Ala Asp Glu Leu Val Glu Leu Ser
                245                 250                 255

Thr Ala Leu Glu His Gln Glu Tyr Ile Thr Phe Leu Glu Asp Leu Lys
            260                 265                 270

Ser Phe Val Lys Ser Gln
        275

<210> SEQ ID NO 12
<211> LENGTH: 661
<212> TYPE: PRT
<213> ORGANISM: Human

<400> SEQUENCE: 12

Arg Ala Leu Arg Arg Ala Pro Ala Leu Ala Ala Val Pro Gly Gly Lys
1               5                   10                  15

Pro Ile Leu Cys Pro Arg Arg Thr Thr Ala Gln Leu Gly Pro Arg Arg
            20                  25                  30

Asn Pro Ala Trp Ser Leu Gln Ala Gly Arg Leu Phe Ser Thr Gln Thr
        35                  40                  45

Ala Glu Asp Lys Glu Glu Pro Leu His Ser Ile Ile Ser Ser Thr Glu
    50                  55                  60

Ser Val Gln Gly Ser Thr Ser Lys His Glu Phe Gln Ala Glu Thr Lys
65                  70                  75                  80

Lys Leu Leu Asp Ile Val Ala Arg Ser Leu Tyr Ser Glu Lys Glu Val
                85                  90                  95

Phe Ile Arg Glu Leu Ile Ser Asn Ala Ser Asp Ala Leu Glu Lys Leu
            100                 105                 110

Arg His Lys Leu Val Ser Asp Gly Gln Ala Leu Pro Glu Met Glu Ile
        115                 120                 125

His Leu Gln Thr Asn Ala Glu Lys Gly Thr Ile Thr Ile Gln Asp Thr
    130                 135                 140

Gly Ile Gly Met Thr Gln Glu Glu Leu Val Ser Asn Leu Gly Thr Ile
145                 150                 155                 160

Ala Arg Ser Gly Ser Lys Ala Phe Leu Asp Ala Leu Gln Asn Gln Ala
                165                 170                 175

Glu Ala Ser Ser Lys Ile Ile Gly Gln Phe Gly Val Gly Phe Tyr Ser
            180                 185                 190

Ala Phe Met Val Ala Asp Arg Val Glu Val Tyr Ser Arg Ser Ala Ala
        195                 200                 205

Pro Gly Ser Leu Gly Tyr Gln Trp Leu Ser Asp Gly Ser Gly Val Phe
    210                 215                 220
```

```
Glu Ile Ala Glu Ala Ser Gly Val Arg Thr Gly Thr Lys Ile Ile Ile
225                 230                 235                 240

His Leu Lys Ser Asp Cys Lys Glu Phe Ser Ser Glu Ala Arg Val Arg
                245                 250                 255

Asp Val Val Thr Lys Tyr Ser Asn Phe Val Ser Phe Pro Leu Tyr Leu
            260                 265                 270

Asn Gly Arg Arg Met Asn Thr Leu Gln Ala Ile Trp Met Met Asp Pro
        275                 280                 285

Lys Asp Val Gly Glu Trp Gln His Glu Glu Phe Tyr Arg Tyr Val Ala
    290                 295                 300

Gln Ala His Asp Lys Pro Arg Tyr Thr Leu His Tyr Lys Thr Asp Ala
305                 310                 315                 320

Pro Leu Asn Ile Arg Ser Ile Phe Tyr Val Pro Asp Met Lys Pro Ser
                325                 330                 335

Met Phe Asp Val Ser Arg Glu Leu Gly Ser Ser Val Ala Leu Tyr Ser
            340                 345                 350

Arg Lys Val Leu Ile Gln Thr Lys Ala Thr Asp Ile Leu Pro Lys Trp
        355                 360                 365

Leu Arg Phe Ile Arg Gly Val Val Asp Ser Glu Asp Ile Pro Leu Asn
    370                 375                 380

Leu Ser Arg Glu Leu Leu Gln Glu Ser Ala Leu Ile Arg Lys Leu Arg
385                 390                 395                 400

Asp Val Leu Gln Gln Arg Leu Ile Lys Phe Phe Ile Asp Gln Ser Lys
                405                 410                 415

Lys Asp Ala Glu Lys Tyr Ala Lys Phe Phe Glu Asp Tyr Gly Leu Phe
            420                 425                 430

Met Arg Glu Gly Ile Val Thr Ala Thr Glu Gln Glu Val Lys Glu Asp
        435                 440                 445

Ile Ala Lys Leu Leu Arg Tyr Glu Ser Ser Ala Leu Pro Ser Gly Gln
    450                 455                 460

Leu Thr Ser Leu Ser Glu Tyr Ala Ser Arg Met Arg Ala Gly Thr Arg
465                 470                 475                 480

Asn Ile Tyr Tyr Leu Cys Ala Pro Asn Arg His Leu Ala Glu His Ser
                485                 490                 495

Pro Tyr Tyr Glu Ala Met Lys Lys Lys Asp Thr Glu Val Leu Phe Cys
            500                 505                 510

Phe Glu Gln Phe Asp Glu Leu Thr Leu Leu His Leu Arg Glu Phe Asp
        515                 520                 525

Lys Lys Lys Leu Ile Ser Val Glu Thr Asp Ile Val Val Asp His Tyr
    530                 535                 540

Lys Glu Glu Lys Phe Glu Asp Arg Ser Pro Ala Ala Glu Cys Leu Ser
545                 550                 555                 560

Glu Lys Glu Thr Glu Glu Leu Met Ala Trp Met Arg Asn Val Leu Gly
                565                 570                 575

Ser Arg Val Thr Asn Val Lys Val Thr Leu Arg Leu Asp Thr His Pro
            580                 585                 590

Ala Met Val Thr Val Leu Glu Met Gly Ala Ala Arg His Phe Leu Arg
        595                 600                 605

Met Gln Gln Leu Ala Lys Thr Gln Glu Glu Arg Ala Gln Leu Leu Gln
    610                 615                 620

Pro Thr Leu Glu Ile Asn Pro Arg His Ala Leu Ile Lys Lys Leu Asn
625                 630                 635                 640

His Cys Ala Gln Ala Ser Leu Ala Trp Leu Ser Cys Trp Trp Ile Arg
```

```
                      645                 650                 655
Tyr Thr Arg Thr Pro
                660

<210> SEQ ID NO 13
<211> LENGTH: 803
<212> TYPE: PRT
<213> ORGANISM: Human

<400> SEQUENCE: 13

Met Arg Ala Leu Trp Val Leu Gly Leu Cys Cys Val Leu Leu Thr Phe
1               5                   10                  15

Gly Ser Val Arg Ala Asp Asp Glu Val Asp Val Asp Gly Thr Val Glu
            20                  25                  30

Glu Asp Leu Gly Lys Ser Arg Glu Gly Ser Arg Thr Asp Asp Glu Val
        35                  40                  45

Val Gln Arg Glu Glu Glu Ala Ile Gln Leu Asp Gly Leu Asn Ala Ser
50                  55                  60

Gln Ile Arg Glu Leu Arg Glu Lys Ser Glu Lys Phe Ala Phe Gln Ala
65                  70                  75                  80

Glu Val Asn Arg Met Met Lys Leu Ile Ile Asn Ser Leu Tyr Lys Asn
                85                  90                  95

Lys Glu Ile Phe Leu Arg Glu Leu Ile Ser Asn Ala Ser Asp Ala Leu
            100                 105                 110

Asp Lys Ile Arg Leu Ile Ser Leu Thr Asp Glu Asn Ala Leu Ser Gly
        115                 120                 125

Asn Glu Glu Leu Thr Val Lys Ile Lys Cys Asp Lys Glu Lys Asn Leu
130                 135                 140

Leu His Val Thr Asp Thr Gly Val Gly Met Thr Arg Glu Glu Leu Val
145                 150                 155                 160

Lys Asn Leu Gly Thr Ile Ala Lys Ser Gly Thr Ser Glu Phe Leu Asn
                165                 170                 175

Lys Met Thr Glu Ala Gln Glu Asp Gly Gln Ser Thr Ser Glu Leu Ile
            180                 185                 190

Gly Gln Phe Gly Val Gly Phe Tyr Ser Ala Phe Leu Val Ala Asp Lys
        195                 200                 205

Val Ile Val Thr Ser Lys His Asn Asn Asp Thr Gln His Ile Trp Glu
210                 215                 220

Ser Asp Ser Asn Glu Phe Ser Val Ile Ala Asp Pro Arg Gly Asn Thr
225                 230                 235                 240

Leu Gly Arg Gly Thr Thr Ile Thr Leu Val Leu Lys Glu Glu Ala Ser
                245                 250                 255

Asp Tyr Leu Glu Leu Asp Thr Ile Lys Asn Leu Val Lys Lys Tyr Ser
            260                 265                 270

Gln Phe Ile Asn Phe Pro Ile Tyr Val Trp Ser Ser Lys Thr Glu Thr
        275                 280                 285

Val Glu Glu Pro Met Glu Glu Glu Ala Ala Lys Glu Glu Lys Glu
290                 295                 300

Glu Ser Asp Asp Glu Ala Ala Val Glu Glu Glu Glu Glu Lys Lys
305                 310                 315                 320

Pro Lys Thr Lys Lys Val Glu Lys Thr Val Trp Asp Trp Glu Leu Met
                325                 330                 335

Asn Asp Ile Lys Pro Ile Trp Gln Arg Pro Ser Lys Glu Val Glu Glu
            340                 345                 350

Asp Glu Tyr Lys Ala Phe Tyr Lys Ser Phe Ser Lys Glu Ser Asp Asp
```

```
                355                 360                 365
Pro Met Ala Tyr Ile His Phe Thr Ala Glu Gly Glu Val Thr Phe Lys
    370                 375                 380

Ser Ile Leu Phe Val Pro Thr Ser Ala Pro Arg Gly Leu Phe Asp Glu
385                 390                 395                 400

Tyr Gly Ser Lys Lys Ser Asp Tyr Ile Lys Leu Tyr Val Arg Arg Val
                405                 410                 415

Phe Ile Thr Asp Asp Phe His Asp Met Met Pro Lys Tyr Leu Asn Phe
            420                 425                 430

Val Lys Gly Val Val Asp Ser Asp Asp Leu Pro Leu Asn Val Ser Arg
        435                 440                 445

Glu Thr Leu Gln Gln His Lys Leu Leu Lys Val Ile Arg Lys Lys Leu
    450                 455                 460

Val Arg Lys Thr Leu Asp Met Ile Lys Lys Ile Ala Asp Asp Lys Tyr
465                 470                 475                 480

Asn Asp Thr Phe Trp Lys Glu Phe Gly Thr Asn Ile Lys Leu Gly Val
                485                 490                 495

Ile Glu Asp His Ser Asn Arg Thr Arg Leu Ala Lys Leu Leu Arg Phe
            500                 505                 510

Gln Ser Ser His His Pro Thr Asp Ile Thr Ser Leu Asp Gln Tyr Val
        515                 520                 525

Glu Arg Met Lys Glu Lys Gln Asp Lys Ile Tyr Phe Met Ala Gly Ser
    530                 535                 540

Ser Arg Lys Glu Ala Glu Ser Ser Pro Phe Val Glu Arg Leu Leu Lys
545                 550                 555                 560

Lys Gly Tyr Glu Val Ile Tyr Leu Thr Glu Pro Val Asp Glu Tyr Cys
                565                 570                 575

Ile Gln Ala Leu Pro Glu Phe Asp Gly Lys Arg Phe Gln Asn Val Ala
            580                 585                 590

Lys Glu Gly Val Lys Phe Asp Glu Ser Glu Lys Thr Lys Glu Ser Arg
        595                 600                 605

Glu Ala Val Glu Lys Glu Phe Glu Pro Leu Leu Asn Trp Met Lys Asp
    610                 615                 620

Lys Ala Leu Lys Asp Lys Ile Glu Lys Ala Val Val Ser Gln Arg Leu
625                 630                 635                 640

Thr Glu Ser Pro Cys Ala Leu Val Ala Ser Gln Tyr Gly Trp Ser Gly
                645                 650                 655

Asn Met Glu Arg Ile Met Lys Ala Gln Ala Tyr Gln Thr Gly Lys Asp
            660                 665                 670

Ile Ser Thr Asn Tyr Tyr Ala Ser Gln Lys Lys Thr Phe Glu Ile Asn
        675                 680                 685

Pro Arg His Pro Leu Ile Arg Asp Met Leu Arg Arg Ile Lys Glu Asp
    690                 695                 700

Glu Asp Asp Lys Thr Val Leu Asp Leu Ala Val Val Leu Phe Glu Thr
705                 710                 715                 720

Ala Thr Leu Arg Ser Gly Tyr Leu Leu Pro Asp Thr Lys Ala Tyr Gly
                725                 730                 735

Asp Arg Ile Glu Arg Met Leu Arg Leu Ser Leu Asn Ile Asp Pro Asp
            740                 745                 750

Ala Lys Val Glu Glu Glu Pro Glu Glu Glu Pro Glu Glu Thr Ala Glu
        755                 760                 765

Asp Thr Thr Glu Asp Thr Glu Gln Asp Glu Asp Glu Glu Met Asp Val
    770                 775                 780
```

```
Gly Thr Asp Glu Glu Glu Thr Ala Lys Glu Ser Thr Ala Glu Lys
785                 790                 795                 800

Asp Glu Leu

<210> SEQ ID NO 14
<211> LENGTH: 724
<212> TYPE: PRT
<213> ORGANISM: Human

<400> SEQUENCE: 14

Met Pro Glu Glu Val His His Gly Glu Glu Val Glu Thr Phe Ala
1               5                   10                  15

Phe Gln Ala Glu Ile Ala Gln Leu Met Ser Leu Ile Ile Asn Thr Phe
            20                  25                  30

Tyr Ser Asn Lys Glu Ile Phe Leu Arg Glu Leu Ile Ser Asn Ala Ser
                35                  40                  45

Asp Ala Leu Asp Lys Ile Arg Tyr Glu Ser Leu Thr Asp Pro Ser Lys
50                  55                  60

Leu Asp Ser Gly Lys Glu Leu Lys Ile Asp Ile Ile Pro Asn Pro Gln
65                  70                  75                  80

Glu Arg Thr Leu Thr Leu Val Asp Thr Gly Ile Gly Met Thr Lys Ala
                85                  90                  95

Asp Leu Ile Asn Asn Leu Gly Thr Ile Ala Lys Ser Gly Thr Lys Ala
            100                 105                 110

Phe Met Glu Ala Leu Gln Ala Gly Ala Asp Ile Ser Met Ile Gly Gln
        115                 120                 125

Phe Gly Val Gly Phe Tyr Ser Ala Tyr Leu Val Ala Glu Lys Val Val
130                 135                 140

Val Ile Arg Lys His Asn Asp Asp Glu Gln Tyr Ala Trp Glu Ser Ser
145                 150                 155                 160

Ala Gly Gly Ser Phe Thr Val Arg Ala Asp His Gly Glu Pro Ile Gly
                165                 170                 175

Met Gly Thr Lys Val Ile Leu His Leu Lys Glu Asp Gln Thr Glu Tyr
            180                 185                 190

Leu Glu Glu Arg Arg Val Lys Glu Val Val Lys Lys His Ser Gln Phe
        195                 200                 205

Ile Gly Tyr Pro Ile Thr Leu Tyr Leu Glu Lys Glu Arg Glu Lys Glu
210                 215                 220

Ile Ser Asp Asp Glu Ala Glu Glu Lys Glu Asp Lys Glu Glu
225                 230                 235                 240

Asp Lys Asp Asp Glu Glu Lys Pro Lys Ile Glu Asp Val Gly Ser Asp
                245                 250                 255

Glu Glu Asp Asp Ser Gly Lys Asp Lys Lys Lys Thr Lys Lys Ile
            260                 265                 270

Lys Glu Lys Tyr Ile Asp Gln Glu Glu Leu Asn Lys Thr Lys Pro Ile
        275                 280                 285

Trp Thr Arg Asn Pro Asp Asp Ile Thr Gln Glu Glu Tyr Gly Glu Phe
290                 295                 300

Tyr Lys Ser Leu Thr Asn Asp Trp Glu Asp His Leu Ala Val Lys His
305                 310                 315                 320

Phe Ser Val Glu Gly Gln Leu Glu Phe Arg Ala Leu Leu Phe Ile Pro
                325                 330                 335

Arg Arg Ala Pro Phe Asp Leu Phe Glu Asn Lys Lys Lys Lys Asn Asn
            340                 345                 350

Ile Lys Leu Tyr Val Arg Arg Val Phe Ile Met Asp Ser Cys Asp Glu
```

```
Leu Ile Pro Glu Tyr Leu Asn Phe Ile Arg Gly Val Val Asp Ser Glu
            355                 360                 365
Asp Leu Pro Leu Asn Ile Ser Arg Glu Met Leu Gln Gln Ser Lys Ile
370                 375                 380
Leu Lys Val Ile Arg Lys Asn Ile Val Lys Lys Cys Leu Glu Leu Phe
385                 390                 395                 400
Ser Glu Leu Ala Glu Asp Lys Glu Asn Tyr Lys Lys Phe Tyr Glu Ala
            405                 410                 415
Phe Ser Lys Asn Leu Lys Leu Gly Ile His Glu Asp Ser Thr Asn Arg
        420                 425                 430
Arg Arg Leu Ser Glu Leu Leu Arg Tyr His Thr Ser Gln Ser Gly Asp
    435                 440                 445
Glu Met Thr Ser Leu Ser Glu Tyr Val Ser Arg Met Lys Glu Thr Gln
450                 455                 460
Lys Ser Ile Tyr Tyr Ile Thr Gly Glu Ser Lys Glu Gln Val Ala Asn
465                 470                 475                 480
Ser Ala Phe Val Glu Arg Val Arg Lys Arg Gly Phe Glu Val Val Tyr
            485                 490                 495
Met Thr Glu Pro Ile Asp Glu Tyr Cys Val Gln Gln Leu Lys Glu Phe
        500                 505                 510
Asp Gly Lys Ser Leu Val Ser Val Thr Lys Glu Gly Leu Glu Leu Pro
    515                 520                 525
Glu Asp Glu Glu Glu Lys Lys Lys Met Glu Glu Ser Lys Ala Lys Phe
530                 535                 540
Glu Asn Leu Cys Lys Leu Met Lys Glu Ile Leu Asp Lys Lys Val Glu
545                 550                 555                 560
Lys Val Thr Ile Ser Asn Arg Leu Val Ser Ser Pro Cys Cys Ile Val
            565                 570                 575
Thr Ser Thr Tyr Gly Trp Thr Ala Asn Met Glu Arg Ile Met Lys Ala
        580                 585                 590
Gln Ala Leu Arg Asp Asn Ser Thr Met Gly Tyr Met Met Ala Lys Lys
    595                 600                 605
His Leu Glu Ile Asn Pro Asp His Pro Ile Val Glu Thr Leu Arg Gln
610                 615                 620
Lys Ala Glu Ala Asp Lys Asn Asp Lys Ala Val Lys Asp Leu Val Val
625                 630                 635                 640
Leu Leu Phe Glu Thr Ala Leu Leu Ser Ser Gly Phe Ser Leu Glu Asp
            645                 650                 655
Pro Gln Thr His Ser Asn Arg Ile Tyr Arg Met Ile Lys Leu Gly Leu
        660                 665                 670
Gly Ile Asp Glu Asp Glu Val Ala Ala Glu Glu Pro Asn Ala Ala Val
    675                 680                 685
Pro Asp Glu Ile Pro Pro Leu Glu Gly Asp Glu Asp Ala Ser Arg Met
690                 695                 700
Glu Glu Val Asp
705                 710                 715                 720

<210> SEQ ID NO 15
<211> LENGTH: 732
<212> TYPE: PRT
<213> ORGANISM: Human

<400> SEQUENCE: 15

Met Pro Glu Glu Thr Gln Thr Gln Asp Gln Pro Met Glu Glu Glu Glu
1               5                   10                  15
```

```
Val Glu Thr Phe Ala Phe Gln Ala Glu Ile Ala Gln Leu Met Ser Leu
            20                  25                  30
Ile Ile Asn Thr Phe Tyr Ser Asn Lys Glu Ile Phe Leu Arg Glu Leu
            35                  40                  45
Ile Ser Asn Ser Ser Asp Ala Leu Asp Lys Ile Arg Tyr Glu Thr Leu
50                  55                  60
Thr Asp Pro Ser Lys Leu Asp Ser Gly Lys Glu Leu His Ile Asn Leu
65                  70                  75                  80
Ile Pro Asn Lys Gln Asp Arg Thr Leu Thr Ile Val Asp Thr Gly Ile
                85                  90                  95
Gly Met Thr Lys Ala Asp Leu Ile Asn Asn Leu Gly Thr Ile Ala Lys
                100                 105                 110
Ser Gly Thr Lys Ala Phe Met Glu Ala Leu Gln Ala Gly Ala Asp Ile
                115                 120                 125
Ser Met Ile Gly Gln Phe Gly Val Gly Phe Tyr Ser Ala Tyr Leu Val
                130                 135                 140
Ala Glu Lys Val Thr Val Ile Thr Lys His Asn Asp Asp Glu Gln Tyr
145                 150                 155                 160
Ala Trp Glu Ser Ser Ala Gly Gly Ser Phe Thr Val Arg Thr Asp Thr
                165                 170                 175
Gly Glu Pro Met Gly Arg Gly Thr Lys Val Ile Leu His Leu Lys Glu
                180                 185                 190
Asp Gln Thr Glu Tyr Leu Glu Glu Arg Arg Ile Lys Glu Ile Val Lys
                195                 200                 205
Lys His Ser Gln Phe Ile Gly Tyr Pro Ile Thr Leu Phe Val Glu Lys
            210                 215                 220
Glu Arg Asp Lys Glu Val Ser Asp Asp Glu Ala Glu Glu Lys Glu Asp
225                 230                 235                 240
Lys Glu Glu Glu Lys Glu Lys Glu Glu Lys Glu Ser Glu Asp Lys Pro
                245                 250                 255
Glu Ile Glu Asp Val Gly Ser Asp Glu Glu Glu Glu Lys Lys Asp Gly
                260                 265                 270
Asp Lys Lys Lys Lys Lys Lys Ile Lys Glu Lys Tyr Ile Asp Gln Glu
            275                 280                 285
Glu Leu Asn Lys Thr Lys Pro Ile Trp Thr Arg Asn Pro Asp Asp Ile
            290                 295                 300
Thr Asn Glu Glu Tyr Gly Glu Phe Tyr Lys Ser Leu Thr Asn Asp Trp
305                 310                 315                 320
Glu Asp His Leu Ala Val Lys His Phe Ser Val Glu Gly Gln Leu Glu
                325                 330                 335
Phe Arg Ala Leu Leu Phe Val Pro Arg Arg Ala Pro Phe Asp Leu Phe
                340                 345                 350
Glu Asn Arg Lys Lys Lys Asn Asn Ile Lys Leu Tyr Val Arg Arg Val
                355                 360                 365
Phe Ile Met Asp Asn Cys Glu Glu Leu Ile Pro Glu Tyr Leu Asn Phe
                370                 375                 380
Ile Arg Gly Val Val Asp Ser Glu Asp Leu Pro Leu Asn Ile Ser Arg
385                 390                 395                 400
Glu Met Leu Gln Gln Ser Lys Ile Leu Lys Val Ile Arg Lys Asn Leu
                405                 410                 415
Val Lys Lys Cys Leu Glu Leu Phe Thr Glu Leu Ala Glu Asp Lys Glu
                420                 425                 430
Asn Tyr Lys Lys Phe Tyr Glu Gln Phe Ser Lys Asn Ile Lys Leu Gly
```

```
                435                 440                 445
Ile His Glu Asp Ser Gln Asn Arg Lys Lys Leu Ser Glu Leu Leu Arg
450                 455                 460

Tyr Tyr Thr Ser Ala Ser Gly Asp Glu Met Val Ser Leu Lys Asp Tyr
465                 470                 475                 480

Cys Thr Arg Met Lys Glu Asn Gln Lys His Ile Tyr Tyr Ile Thr Gly
                485                 490                 495

Glu Thr Lys Asp Gln Val Ala Asn Ser Ala Phe Val Glu Arg Leu Arg
                500                 505                 510

Lys His Gly Leu Glu Val Ile Tyr Met Ile Glu Pro Ile Asp Glu Tyr
                515                 520                 525

Cys Val Gln Gln Leu Lys Glu Phe Glu Gly Lys Thr Leu Val Ser Val
                530                 535                 540

Thr Lys Glu Gly Leu Glu Leu Pro Glu Asp Glu Glu Lys Lys Lys
545                 550                 555                 560

Gln Glu Glu Lys Lys Thr Lys Phe Glu Asn Leu Cys Lys Ile Met Lys
                565                 570                 575

Asp Ile Leu Glu Lys Lys Val Glu Lys Val Val Ser Asn Arg Leu
                580                 585                 590

Val Thr Ser Pro Cys Cys Ile Val Thr Ser Thr Tyr Gly Trp Thr Ala
                595                 600                 605

Asn Met Glu Arg Ile Met Lys Ala Gln Ala Leu Arg Asp Asn Ser Thr
610                 615                 620

Met Gly Tyr Met Ala Ala Lys Lys His Leu Glu Ile Asn Pro Asp His
625                 630                 635                 640

Ser Ile Ile Glu Thr Leu Arg Gln Lys Ala Glu Ala Asp Lys Asn Asp
                645                 650                 655

Lys Ser Val Lys Asp Leu Val Ile Leu Leu Tyr Glu Thr Ala Leu Leu
                660                 665                 670

Ser Ser Gly Phe Ser Leu Glu Asp Pro Gln Thr His Ala Asn Arg Ile
                675                 680                 685

Tyr Arg Met Ile Lys Leu Gly Leu Gly Ile Asp Glu Asp Asp Pro Thr
690                 695                 700

Ala Asp Asp Thr Ser Ala Ala Val Thr Glu Glu Met Pro Pro Leu Glu
705                 710                 715                 720

Gly Asp Asp Asp Thr Ser Arg Met Glu Glu Val Asp
                725                 730

<210> SEQ ID NO 16
<211> LENGTH: 573
<212> TYPE: PRT
<213> ORGANISM: Human

<400> SEQUENCE: 16

Met Leu Arg Leu Pro Thr Val Phe Arg Gln Met Arg Pro Val Ser Arg
1               5                   10                  15

Val Leu Ala Pro His Leu Thr Arg Ala Tyr Ala Lys Asp Val Lys Phe
                20                  25                  30

Gly Ala Asp Ala Arg Ala Leu Met Leu Gln Gly Val Asp Leu Leu Ala
            35                  40                  45

Asp Ala Val Ala Val Thr Met Gly Pro Lys Gly Arg Thr Val Ile Ile
        50                  55                  60

Glu Gln Ser Trp Gly Ser Pro Lys Val Thr Lys Asp Gly Val Thr Val
65                  70                  75                  80

Ala Lys Ser Ile Asp Leu Lys Asp Lys Tyr Lys Asn Ile Gly Ala Lys
```

```
                85                  90                  95
Leu Val Gln Asp Val Ala Asn Asn Thr Asn Glu Glu Ala Gly Asp Gly
            100                 105                 110

Thr Thr Thr Ala Thr Val Leu Ala Arg Ser Ile Ala Lys Glu Gly Phe
        115                 120                 125

Glu Lys Ile Ser Lys Gly Ala Asn Pro Val Glu Ile Arg Arg Gly Val
    130                 135                 140

Met Leu Ala Val Asp Ala Val Ile Ala Glu Leu Lys Lys Gln Ser Lys
145                 150                 155                 160

Pro Val Thr Thr Pro Glu Glu Ile Ala Gln Val Ala Thr Ile Ser Ala
                165                 170                 175

Asn Gly Asp Lys Glu Ile Gly Asn Ile Ile Ser Asp Ala Met Lys Lys
            180                 185                 190

Val Gly Arg Lys Gly Val Ile Thr Val Lys Asp Gly Lys Thr Leu Asn
        195                 200                 205

Asp Glu Leu Glu Ile Ile Glu Gly Met Lys Phe Asp Arg Gly Tyr Ile
    210                 215                 220

Ser Pro Tyr Phe Ile Asn Thr Ser Lys Gly Gln Lys Cys Glu Phe Gln
225                 230                 235                 240

Asp Ala Tyr Val Leu Leu Ser Glu Lys Lys Ile Ser Ser Ile Gln Ser
                245                 250                 255

Ile Val Pro Ala Leu Glu Ile Ala Asn Ala His Arg Lys Pro Leu Val
            260                 265                 270

Ile Ile Ala Glu Asp Val Asp Gly Glu Ala Leu Ser Thr Leu Val Leu
        275                 280                 285

Asn Arg Leu Lys Val Gly Leu Gln Val Val Ala Val Lys Ala Pro Gly
    290                 295                 300

Phe Gly Asp Asn Arg Lys Asn Gln Leu Lys Asp Met Ala Ile Ala Thr
305                 310                 315                 320

Gly Gly Ala Val Phe Gly Glu Glu Gly Leu Thr Leu Asn Leu Glu Asp
                325                 330                 335

Val Gln Pro His Asp Leu Gly Lys Val Gly Glu Val Ile Val Thr Lys
            340                 345                 350

Asp Asp Ala Met Leu Leu Lys Gly Lys Gly Asp Lys Ala Gln Ile Glu
        355                 360                 365

Lys Arg Ile Gln Glu Ile Ile Glu Gln Leu Asp Val Thr Thr Ser Glu
    370                 375                 380

Tyr Glu Lys Glu Lys Leu Asn Glu Arg Leu Ala Lys Leu Ser Asp Gly
385                 390                 395                 400

Val Ala Val Leu Lys Val Gly Gly Thr Ser Asp Val Glu Val Asn Glu
                405                 410                 415

Lys Lys Asp Arg Val Thr Asp Ala Leu Asn Ala Thr Arg Ala Ala Val
            420                 425                 430

Glu Glu Gly Ile Val Leu Gly Gly Gly Cys Ala Leu Leu Arg Cys Ile
        435                 440                 445

Pro Ala Leu Asp Ser Leu Thr Pro Ala Asn Glu Asp Gln Lys Ile Gly
    450                 455                 460

Ile Glu Ile Ile Lys Arg Thr Leu Lys Ile Pro Ala Met Thr Ile Ala
465                 470                 475                 480

Lys Asn Ala Gly Val Glu Gly Ser Leu Ile Val Glu Lys Ile Met Gln
                485                 490                 495

Ser Ser Ser Glu Val Gly Tyr Asp Ala Met Ala Gly Asp Phe Val Asn
            500                 505                 510
```

Met Val Glu Lys Gly Ile Ile Asp Pro Thr Lys Val Val Arg Thr Ala
            515                 520                 525

Leu Leu Asp Ala Ala Gly Val Ala Ser Leu Leu Thr Thr Ala Glu Val
        530                 535                 540

Val Val Thr Glu Ile Pro Lys Glu Glu Lys Asp Pro Gly Met Gly Ala
545                 550                 555                 560

Met Gly Gly Met Gly Gly Gly Met Gly Gly Met Phe
                565                 570

<210> SEQ ID NO 17
<211> LENGTH: 215
<212> TYPE: PRT
<213> ORGANISM: Human

<400> SEQUENCE: 17

Met Gly Lys Gly Asp Pro Lys Lys Pro Arg Lys Met Ser Ser Tyr
1               5                   10                  15

Ala Phe Phe Val Gln Thr Cys Arg Glu Glu His Lys Lys Lys His Pro
            20                  25                  30

Asp Ala Ser Val Asn Phe Ser Glu Phe Ser Lys Lys Cys Ser Glu Arg
        35                  40                  45

Trp Lys Thr Met Ser Ala Lys Glu Lys Gly Lys Phe Glu Asp Met Ala
    50                  55                  60

Lys Ala Asp Lys Ala Arg Tyr Glu Arg Glu Met Lys Thr Tyr Ile Pro
65                  70                  75                  80

Pro Lys Gly Glu Thr Lys Lys Phe Lys Asp Pro Asn Ala Pro Lys
                85                  90                  95

Arg Pro Pro Ser Ala Phe Phe Leu Phe Cys Ser Glu Tyr Arg Pro Lys
            100                 105                 110

Ile Lys Gly Glu His Pro Gly Leu Ser Ile Gly Asp Val Ala Lys Lys
        115                 120                 125

Leu Gly Glu Met Trp Asn Asn Thr Ala Ala Asp Lys Gln Pro Tyr
    130                 135                 140

Glu Lys Lys Ala Glu Lys Leu Lys Glu Lys Tyr Glu Lys Asp Ile Ala
145                 150                 155                 160

Ala Tyr Arg Ala Lys Gly Lys Pro Asp Ala Ala Lys Lys Gly Val Val
                165                 170                 175

Lys Ala Glu Lys Ser Lys Lys Lys Glu Glu Glu Gly Glu Glu
            180                 185                 190

Asp Glu Glu Asp Glu Glu Glu Glu Asp Glu Glu Asp Glu Asp Glu
        195                 200                 205

Glu Glu Asp Asp Asp Asp Glu
    210                 215

<210> SEQ ID NO 18
<211> LENGTH: 1087
<212> TYPE: PRT
<213> ORGANISM: Human

<400> SEQUENCE: 18

Met Met Thr Ser Val Gly Thr Asn Arg Ala Arg Gly Asn Trp Glu Gln
1               5                   10                  15

Pro Gln Asn Gln Asn Gln Thr Gln His Lys Gln Arg Pro Gln Ala Thr
            20                  25                  30

Ala Glu Gln Ile Arg Leu Ala Gln Met Ile Ser Asp His Asn Asp Ala
        35                  40                  45

Asp Phe Glu Glu Lys Val Lys Gln Leu Ile Asp Ile Thr Gly Lys Asn

```
                50                  55                  60
Gln Asp Glu Cys Val Ile Ala Leu His Asp Cys Asn Gly Asp Val Asn
 65                  70                  75                  80

Arg Ala Ile Asn Val Leu Leu Glu Gly Asn Pro Asp Thr His Ser Trp
                 85                  90                  95

Glu Met Val Gly Lys Lys Gly Val Ser Gly Gln Lys Asp Gly Gly
                100                 105                 110

Gln Thr Glu Ser Asn Glu Glu Gly Lys Glu Asn Arg Asp Arg Asp Arg
                115                 120                 125

Asp Tyr Ser Arg Arg Arg Gly Pro Pro Arg Arg Gly Arg Gly Ala
    130                 135                 140

Ser Arg Gly Arg Glu Phe Arg Gly Gln Glu Asn Gly Leu Asp Gly Thr
145                 150                 155                 160

Lys Ser Gly Gly Pro Ser Gly Arg Gly Thr Glu Arg Gly Arg Gly
                165                 170                 175

Arg Gly Arg Gly Arg Gly Gly Ser Gly Arg Arg Gly Gly Arg Phe Ser
                180                 185                 190

Ala Gln Gly Met Gly Thr Phe Asn Pro Ala Asp Tyr Ala Glu Pro Ala
                195                 200                 205

Asn Thr Asp Asp Asn Tyr Gly Asn Ser Ser Gly Asn Thr Trp Asn Asn
210                 215                 220

Thr Gly His Phe Glu Pro Asp Asp Gly Thr Ser Ala Trp Arg Thr Ala
225                 230                 235                 240

Thr Glu Glu Trp Gly Thr Glu Asp Trp Asn Glu Asp Leu Ser Glu Thr
                245                 250                 255

Lys Ile Phe Thr Ala Ser Asn Val Ser Ser Val Pro Leu Pro Ala Glu
                260                 265                 270

Asn Val Thr Ile Thr Ala Gly Gln Arg Ile Asp Leu Ala Val Leu Leu
                275                 280                 285

Gly Lys Thr Pro Ser Thr Met Glu Asn Asp Ser Ser Asn Leu Asp Pro
                290                 295                 300

Ser Gln Ala Pro Ser Leu Ala Gln Pro Leu Val Phe Ser Asn Ser Lys
305                 310                 315                 320

Gln Thr Ala Ile Ser Gln Pro Ala Ser Gly Asn Thr Phe Ser His His
                325                 330                 335

Ser Met Val Ser Met Leu Gly Lys Gly Phe Gly Asp Val Gly Glu Ala
                340                 345                 350

Lys Gly Gly Ser Thr Thr Gly Ser Gln Phe Leu Glu Gln Phe Lys Thr
                355                 360                 365

Ala Gln Ala Leu Ala Gln Leu Ala Ala Gln His Ser Gln Ser Gly Ser
                370                 375                 380

Thr Thr Thr Ser Ser Trp Asp Met Gly Ser Thr Thr Gln Ser Pro Ser
385                 390                 395                 400

Leu Val Gln Tyr Asp Leu Lys Asn Pro Ser Asp Ser Ala Val His Ser
                405                 410                 415

Pro Phe Thr Lys Arg Gln Ala Phe Thr Pro Ser Ser Thr Met Met Glu
                420                 425                 430

Val Phe Leu Gln Glu Lys Ser Pro Ala Val Ala Thr Ser Thr Ala Ala
                435                 440                 445

Pro Pro Pro Pro Ser Pro Leu Pro Ser Lys Ser Thr Ser Ala Pro
                450                 455                 460

Gln Met Ser Pro Gly Ser Ser Asp Asn Gln Ser Ser Ser Pro Gln Pro
465                 470                 475                 480
```

-continued

```
Ala His Gln Lys Leu Lys Gln Gln Lys Lys Ala Ser Leu Thr Ser
                485                 490                 495

Lys Ile Pro Ala Leu Ala Val Glu Met Pro Gly Ser Ala Asp Ile Ser
            500                 505                 510

Gly Leu Asn Leu Gln Phe Gly Ala Leu Gln Phe Gly Ser Glu Pro Val
        515                 520                 525

Leu Ser Asp Tyr Glu Ser Thr Pro Thr Thr Ser Ala Ser Ser Ser Gln
    530                 535                 540

Ala Pro Ser Ser Leu Tyr Thr Ser Thr Ala Ser Glu Ser Ser Ser Thr
545                 550                 555                 560

Ile Ser Ser Asn Gln Ser Gln Glu Ser Gly Tyr Gln Ser Gly Pro Ile
                565                 570                 575

Gln Ser Thr Thr Tyr Thr Ser Gln Asn Asn Ala Gln Gly Pro Leu Tyr
            580                 585                 590

Glu Gln Arg Ser Thr Gln Thr Arg Arg Tyr Pro Ser Ser Ile Ser Ser
        595                 600                 605

Ser Pro Gln Lys Asp Leu Thr Gln Ala Lys Asn Gly Phe Ser Ser Val
    610                 615                 620

Gln Ala Thr Gln Leu Gln Thr Thr Gln Ser Val Glu Gly Ala Thr Gly
625                 630                 635                 640

Ser Ala Val Lys Ser Asp Ser Pro Ser Thr Ser Ser Ile Pro Pro Leu
                645                 650                 655

Asn Glu Thr Val Ser Ala Ala Ser Leu Leu Thr Thr Asn Gln His
            660                 665                 670

Ser Ser Ser Leu Gly Gly Leu Ser His Ser Glu Glu Ile Pro Asn Thr
        675                 680                 685

Thr Thr Thr Gln His Ser Ser Thr Leu Ser Thr Gln Gln Asn Thr Leu
    690                 695                 700

Ser Ser Ser Thr Ser Ser Gly Arg Thr Ser Thr Ser Thr Leu Leu His
705                 710                 715                 720

Thr Ser Val Glu Ser Glu Ala Asn Leu His Ser Ser Ser Ser Thr Phe
                725                 730                 735

Ser Thr Ser Ser Thr Val Ser Ala Pro Pro Val Val Ser Val
            740                 745                 750

Ser Ser Ser Leu Asn Ser Gly Ser Ser Leu Gly Leu Ser Leu Gly Ser
        755                 760                 765

Asn Ser Thr Val Thr Ala Ser Thr Arg Ser Ser Val Ala Thr Thr Ser
    770                 775                 780

Gly Lys Ala Pro Pro Asn Leu Pro Pro Gly Val Pro Pro Leu Leu Pro
785                 790                 795                 800

Asn Pro Tyr Ile Met Ala Pro Gly Leu Leu His Ala Tyr Pro Pro Gln
                805                 810                 815

Val Tyr Gly Tyr Asp Asp Leu Gln Met Leu Gln Thr Arg Phe Pro Leu
            820                 825                 830

Asp Tyr Tyr Ser Ile Pro Phe Pro Thr Pro Thr Pro Leu Thr Gly
        835                 840                 845

Arg Asp Gly Ser Leu Ala Ser Asn Pro Tyr Ser Gly Asp Leu Thr Lys
    850                 855                 860

Phe Gly Arg Gly Asp Ala Ser Ser Pro Ala Pro Ala Thr Thr Leu Ala
865                 870                 875                 880

Gln Pro Gln Gln Asn Gln Thr Gln Thr His His Thr Thr Gln Thr
                885                 890                 895

Phe Leu Asn Pro Ala Leu Pro Pro Gly Tyr Ser Tyr Thr Ser Leu Pro
            900                 905                 910
```

-continued

Tyr Tyr Thr Gly Val Pro Gly Leu Pro Ser Thr Phe Gln Tyr Gly Pro
            915                 920                 925

Ala Val Phe Pro Val Ala Pro Thr Ser Ser Lys Gln His Gly Val Asn
        930                 935                 940

Val Ser Val Asn Ala Ser Ala Thr Pro Phe Gln Pro Ser Gly Tyr
945                 950                 955                 960

Gly Ser His Gly Tyr Asn Thr Gly Val Ser Val Thr Ser Ser Asn Thr
                965                 970                 975

Gly Val Pro Asp Ile Ser Gly Ser Val Tyr Ser Lys Thr Gln Gln Ser
                980                 985                 990

Phe Glu Lys Gln Gly Phe His Ser Gly Thr Pro Ala Ala Ser Phe Asn
            995                 1000                1005

Leu Pro Ser Ala Leu Gly Ser Gly Gly Pro Ile Asn Pro Ala Thr
        1010                1015                1020

Ala Ala Ala Tyr Pro Pro Ala Pro Phe Met His Ile Leu Thr Pro
        1025                1030                1035

His Gln Gln Pro His Ser Gln Ile Leu His His His Leu Gln Gln
        1040                1045                1050

Asp Gly Gln Thr Gly Ser Gly Gln Arg Ser Gln Thr Ser Ser Ile
        1055                1060                1065

Pro Gln Lys Pro Gln Thr Asn Lys Ser Ala Tyr Asn Ser Tyr Ser
        1070                1075                1080

Trp Gly Ala Asn
        1085

<210> SEQ ID NO 19
<211> LENGTH: 806
<212> TYPE: PRT
<213> ORGANISM: Human

<400> SEQUENCE: 19

Met Ala Ser Gly Ala Asp Ser Lys Gly Asp Asp Leu Ser Thr Ala Ile
1               5                   10                  15

Leu Lys Gln Lys Asn Arg Pro Asn Arg Leu Ile Val Asp Glu Ala Ile
            20                  25                  30

Asn Glu Asp Asn Ser Val Val Ser Leu Ser Gln Pro Lys Met Asp Glu
        35                  40                  45

Leu Gln Leu Phe Arg Gly Asp Thr Val Leu Leu Lys Gly Lys Lys Arg
    50                  55                  60

Arg Glu Ala Val Cys Ile Val Leu Ser Asp Asp Thr Cys Ser Asp Glu
65                  70                  75                  80

Lys Ile Arg Met Asn Arg Val Val Arg Asn Asn Leu Arg Val Arg Leu
                85                  90                  95

Gly Asp Val Ile Ser Ile Gln Pro Cys Pro Asp Val Lys Tyr Gly Lys
            100                 105                 110

Arg Ile His Val Leu Pro Ile Asp Asp Thr Val Glu Gly Ile Thr Gly
        115                 120                 125

Asn Leu Phe Glu Val Tyr Leu Lys Pro Tyr Phe Leu Glu Ala Tyr Arg
    130                 135                 140

Pro Ile Arg Lys Gly Asp Ile Phe Leu Val Arg Gly Gly Met Arg Ala
145                 150                 155                 160

Val Glu Phe Lys Val Val Glu Thr Asp Pro Ser Pro Tyr Cys Ile Val
                165                 170                 175

Ala Pro Asp Thr Val Ile His Cys Glu Gly Glu Pro Ile Lys Arg Glu
            180                 185                 190

```
Asp Glu Glu Glu Ser Leu Asn Glu Val Gly Tyr Asp Asp Ile Gly Gly
            195                 200                 205

Cys Arg Lys Gln Leu Ala Gln Ile Lys Glu Met Val Glu Leu Pro Leu
        210                 215                 220

Arg His Pro Ala Leu Phe Lys Ala Ile Gly Val Lys Pro Pro Arg Gly
225                 230                 235                 240

Ile Leu Leu Tyr Gly Pro Pro Gly Thr Gly Lys Thr Leu Ile Ala Arg
                245                 250                 255

Ala Val Ala Asn Glu Thr Gly Ala Phe Phe Phe Leu Ile Asn Gly Pro
            260                 265                 270

Glu Ile Met Ser Lys Leu Ala Gly Glu Ser Glu Ser Asn Leu Arg Lys
        275                 280                 285

Ala Phe Glu Glu Ala Lys Asn Ala Pro Ala Ile Ile Phe Ile Asp
290                 295                 300

Glu Leu Asp Ala Ile Ala Pro Lys Arg Glu Lys Thr His Gly Glu Val
305                 310                 315                 320

Glu Arg Arg Ile Val Ser Gln Leu Leu Thr Leu Met Asp Gly Leu Lys
                325                 330                 335

Gln Arg Ala His Val Ile Val Met Ala Ala Thr Asn Arg Pro Asn Ser
            340                 345                 350

Ile Asp Pro Ala Leu Arg Arg Phe Gly Arg Phe Asp Arg Glu Val Asp
        355                 360                 365

Ile Gly Ile Pro Asp Ala Thr Gly Arg Leu Glu Ile Leu Gln Ile His
370                 375                 380

Thr Lys Asn Met Lys Leu Ala Asp Asp Val Asp Leu Glu Gln Val Ala
385                 390                 395                 400

Asn Glu Thr His Gly His Val Gly Ala Asp Leu Ala Ala Leu Cys Ser
                405                 410                 415

Glu Ala Ala Leu Gln Ala Ile Arg Lys Lys Met Asp Leu Ile Asp Leu
            420                 425                 430

Glu Asp Glu Thr Ile Asp Ala Glu Val Met Asn Ser Leu Ala Val Thr
        435                 440                 445

Met Asp Asp Phe Arg Trp Ala Leu Ser Gln Ser Asn Pro Ser Ala Leu
450                 455                 460

Arg Glu Thr Val Val Glu Val Pro Gln Val Thr Trp Glu Asp Ile Gly
465                 470                 475                 480

Gly Leu Glu Asp Val Lys Arg Glu Leu Gln Glu Leu Val Gln Tyr Pro
                485                 490                 495

Val Glu His Pro Asp Lys Phe Leu Lys Phe Gly Met Thr Pro Ser Lys
            500                 505                 510

Gly Val Leu Phe Tyr Gly Pro Pro Gly Cys Gly Lys Thr Leu Leu Ala
        515                 520                 525

Lys Ala Ile Ala Asn Glu Cys Gln Ala Asn Phe Ile Ser Ile Lys Gly
530                 535                 540

Pro Glu Leu Leu Thr Met Trp Phe Gly Glu Ser Glu Ala Asn Val Arg
545                 550                 555                 560

Glu Ile Phe Asp Lys Ala Arg Gln Ala Ala Pro Cys Val Leu Phe Phe
                565                 570                 575

Asp Glu Leu Asp Ser Ile Ala Lys Ala Arg Gly Gly Asn Ile Gly Asp
            580                 585                 590

Gly Gly Gly Ala Ala Asp Arg Val Ile Asn Gln Ile Leu Thr Glu Met
        595                 600                 605
```

Asp Gly Met Ser Thr Lys Lys Asn Val Phe Ile Ile Gly Ala Thr Asn
610                 615                 620

Arg Pro Asp Ile Ile Asp Pro Ala Ile Leu Arg Pro Gly Arg Leu Asp
625                 630                 635                 640

Gln Leu Ile Tyr Ile Pro Leu Pro Asp Glu Lys Ser Arg Val Ala Ile
                645                 650                 655

Leu Lys Ala Asn Leu Arg Lys Ser Pro Val Ala Lys Asp Val Asp Leu
            660                 665                 670

Glu Phe Leu Ala Lys Met Thr Asn Gly Phe Ser Gly Ala Asp Leu Thr
        675                 680                 685

Glu Ile Cys Gln Arg Ala Cys Lys Leu Ala Ile Arg Glu Ser Ile Glu
690                 695                 700

Ser Glu Ile Arg Arg Glu Arg Glu Arg Gln Thr Asn Pro Ser Ala Met
705                 710                 715                 720

Glu Val Glu Glu Asp Asp Pro Val Pro Glu Ile Arg Arg Asp His Phe
                725                 730                 735

Glu Glu Ala Met Arg Phe Ala Arg Arg Ser Val Ser Asp Asn Asp Ile
            740                 745                 750

Arg Lys Tyr Glu Met Phe Ala Gln Thr Leu Gln Gln Ser Arg Gly Phe
        755                 760                 765

Gly Ser Phe Arg Phe Pro Ser Gly Asn Gln Gly Gly Ala Gly Pro Ser
770                 775                 780

Gln Gly Ser Gly Gly Gly Thr Gly Gly Ser Val Tyr Thr Glu Asp Asn
785                 790                 795                 800

Asp Asp Asp Leu Tyr Gly
                805

<210> SEQ ID NO 20
<211> LENGTH: 260
<212> TYPE: PRT
<213> ORGANISM: Human

<400> SEQUENCE: 20

Met Val Lys Val Lys Val Glu Val Asn Gly Phe Gly His Thr Gly Arg
1               5                   10                  15

Leu Val Thr Arg Ala Ala Phe Asn Ser Gly Lys Val Asp Ile Val Thr
            20                  25                  30

Ile Asn Asp Pro Phe Ile Asp Leu Asn Tyr Pro Phe Ile Asp Leu Asn
        35                  40                  45

Tyr Met Ile Tyr Met Phe Gln Tyr Asp Ser Met Ala Asn Ser Met Ala
    50                  55                  60

Pro Ser Arg Leu Arg Met Gly Ser Leu Ser Ser Arg Glu Ile Pro Ser
65                  70                  75                  80

Pro Ser Ser Arg Ser Glu Ile Pro Pro Lys Ser Asn Gly Gly Glu Ala
                85                  90                  95

Lys Arg Ile Ile Ile Ser Ala Pro Ser Ala Asp Ala Pro Met Phe Met
            100                 105                 110

Met Gly Ile Asn Arg Glu Lys Tyr Asp Asn Ser Leu Glu Ile Ile Ser
        115                 120                 125

Asn Ala Ser Cys Thr Thr Asn Cys Leu Ala Pro Leu Ala Lys Val Ile
    130                 135                 140

His Asp Asn Phe Gly Ile Met Glu Gly Leu Met Thr Thr Val His Ala
145                 150                 155                 160

```
Ile Ala Ala Thr Gln Lys Thr Val Asp Ser Pro Ser Gly Lys Leu Trp
            165                 170                 175

Cys Asp Gly Cys Arg Ala Leu Gln Asn Ile Ile Pro Ala Ser Thr Gly
            180                 185                 190

Ser Ser Leu Ala Lys Pro Ser Val Pro Thr Thr Asn Val Ser Val
            195                 200                 205

Val Asp Leu Thr Cys His Leu Glu Lys Pro Ala Lys Tyr Asp Asp Ile
210                 215                 220

Lys Lys Trp Cys Ser Arg His Gln Lys Ala Pro Ser Arg Ala Ser Trp
225                 230                 235                 240

Ala Thr Leu Ser Thr Cys Asn Arg Val Val Asp Leu Met Ala His Met
            245                 250                 255

Ala Ser Lys Glu
            260

<210> SEQ ID NO 21
<211> LENGTH: 279
<212> TYPE: PRT
<213> ORGANISM: Human

<400> SEQUENCE: 21

Met Asn Lys Val Glu Leu Glu Ser Arg Leu Glu Gly Leu Thr Asp Glu
1               5                   10                  15

Ile Asn Phe Leu Arg Gln Leu Tyr Glu Glu Leu Arg Glu Leu Gln
            20                  25                  30

Ser Gln Ile Ser Asp Thr Ser Val Val Leu Ser Met Asp Asn Ser Arg
            35                  40                  45

Ser Leu Asp Met Asp Ser Ile Ile Ala Glu Val Lys Ala Gln Tyr Glu
        50                  55                  60

Asp Ile Ala Asn Arg Ser Arg Ala Glu Ala Glu Ser Met Tyr Gln Ile
65                  70                  75                  80

Lys Tyr Glu Glu Leu Gln Ser Leu Ala Gly Lys His Gly Asp Asp Leu
                85                  90                  95

Arg Arg Thr Lys Thr Glu Ile Ser Glu Met Asn Arg Asn Ile Ser Arg
            100                 105                 110

Leu Gln Ala Glu Ile Glu Gly Leu Lys Gly Gln Arg Ala Ser Leu Glu
            115                 120                 125

Ala Ala Ile Ala Asp Ala Glu Gln Arg Gly Glu Leu Ala Ile Lys Asp
        130                 135                 140

Ala Asn Ala Lys Leu Ser Glu Leu Glu Ala Ala Leu Gln Arg Ala Lys
145                 150                 155                 160

Gln Asp Met Ala Arg Gln Leu Arg Glu Tyr Gln Glu Leu Met Asn Val
                165                 170                 175

Lys Leu Ala Met Asp Ile Glu Ile Ala Thr Tyr Arg Lys Leu Leu Glu
            180                 185                 190

Gly Glu Glu Ser Arg Leu Glu Ser Gly Met Gln Asn Met Ser Ile His
            195                 200                 205

Thr Lys Thr Thr Gly Gly Tyr Ala Gly Gly Leu Ser Ser Ala Tyr Gly
        210                 215                 220

Gly Leu Ala Ser Pro Gly Leu Ser Tyr Ser Leu Gly Ser Ser Phe Gly
225                 230                 235                 240

Ser Gly Ala Gly Ser Ser Ser Phe Ser Arg Thr Ser Ser Ser Arg Ala
                245                 250                 255

Val Val Val Lys Lys Ile Glu Thr Arg Asp Gly Lys Leu Val Ser Glu
            260                 265                 270
```

Ser Ser Asp Val Leu Pro Lys
        275

<210> SEQ ID NO 22
<211> LENGTH: 577
<212> TYPE: PRT
<213> ORGANISM: Human

<400> SEQUENCE: 22

Met Asn Lys Leu Tyr Ile Gly Asn Leu Asn Glu Ser Val Thr Pro Ala
1               5                   10                  15

Asp Leu Glu Lys Val Phe Ala Glu His Lys Ile Ser Tyr Ser Gly Gln
            20                  25                  30

Phe Leu Val Lys Ser Gly Tyr Ala Phe Val Asp Cys Pro Asp Glu His
        35                  40                  45

Trp Ala Met Lys Ala Ile Glu Thr Phe Ser Gly Lys Val Glu Leu Gln
    50                  55                  60

Gly Lys Arg Leu Glu Ile Glu His Ser Val Pro Lys Lys Gln Arg Ser
65                  70                  75                  80

Arg Lys Ile Gln Ile Arg Asn Ile Pro Pro Gln Leu Arg Trp Glu Val
                85                  90                  95

Leu Asp Ser Leu Leu Ala Gln Tyr Gly Thr Val Glu Asn Cys Glu Gln
            100                 105                 110

Val Asn Thr Glu Ser Glu Thr Ala Val Val Asn Val Thr Tyr Ser Asn
        115                 120                 125

Arg Glu Gln Thr Arg Gln Ala Ile Met Lys Leu Asn Gly His Gln Leu
    130                 135                 140

Glu Asn His Ala Leu Lys Val Ser Tyr Ile Pro Asp Glu Gln Ile Ala
145                 150                 155                 160

Gln Gly Pro Glu Asn Gly Arg Arg Gly Gly Phe Gly Ser Arg Gly Gln
                165                 170                 175

Pro Arg Gln Gly Ser Pro Val Ala Ala Gly Ala Pro Ala Lys Gln Gln
            180                 185                 190

Gln Val Asp Ile Pro Leu Arg Leu Leu Val Pro Thr Gln Tyr Val Gly
        195                 200                 205

Ala Ile Ile Gly Lys Glu Gly Ala Thr Ile Arg Asn Ile Thr Lys Gln
    210                 215                 220

Thr Gln Ser Lys Ile Asp Val His Arg Lys Glu Asn Ala Gly Ala Ala
225                 230                 235                 240

Glu Lys Ala Ile Ser Val His Ser Thr Pro Glu Gly Cys Ser Ser Ala
                245                 250                 255

Cys Lys Met Ile Leu Glu Ile Met His Lys Glu Ala Lys Asp Thr Lys
            260                 265                 270

Thr Ala Asp Glu Val Pro Leu Lys Ile Leu Ala His Asn Asn Phe Val
        275                 280                 285

Gly Arg Leu Ile Gly Lys Glu Gly Arg Asn Leu Lys Lys Val Glu Gln
    290                 295                 300

Asp Thr Glu Thr Lys Ile Thr Ile Ser Ser Leu Gln Asp Leu Thr Leu
305                 310                 315                 320

Tyr Asn Pro Glu Arg Thr Ile Thr Val Lys Gly Ala Ile Glu Asn Cys
                325                 330                 335

Cys Arg Ala Glu Gln Glu Ile Met Lys Lys Val Arg Glu Ala Tyr Glu
            340                 345                 350

Asn Asp Val Ala Ala Met Ser Leu Gln Ser His Leu Ile Pro Gly Leu
        355                 360                 365

-continued

Asn Leu Ala Ala Val Gly Leu Phe Pro Ala Ser Ser Ala Val Pro
    370                 375                 380

Pro Pro Pro Ser Ser Val Thr Gly Ala Ala Pro Tyr Ser Ser Phe Met
385                 390                 395                 400

Gln Ala Pro Glu Gln Glu Met Val Gln Val Phe Ile Pro Ala Gln Ala
                405                 410                 415

Val Gly Ala Ile Ile Gly Lys Lys Gly Gln His Ile Lys Gln Leu Ser
            420                 425                 430

Arg Phe Ala Ser Ala Ser Ile Lys Ile Ala Pro Pro Glu Thr Pro Asp
        435                 440                 445

Ser Lys Val Arg Met Val Ile Ile Thr Gly Pro Pro Glu Ala Gln Phe
    450                 455                 460

Lys Ala Gln Gly Arg Ile Tyr Gly Lys Leu Lys Glu Glu Asn Phe Phe
465                 470                 475                 480

Gly Pro Lys Glu Glu Val Lys Leu Glu Thr His Ile Arg Val Pro Ala
                485                 490                 495

Ser Ala Ala Gly Arg Val Ile Gly Lys Gly Gly Lys Thr Val Asn Glu
            500                 505                 510

Leu Gln Asn Leu Thr Ala Ala Glu Val Val Val Pro Arg Asp Gln Thr
        515                 520                 525

Pro Asp Glu Asn Asp Gln Val Ile Val Lys Ile Ile Gly His Phe Tyr
    530                 535                 540

Ala Ser Gln Met Ala Gln Arg Lys Ile Arg Asp Ile Leu Ala Gln Val
545                 550                 555                 560

Lys Gln Gln His Gln Lys Gly Gln Ser Asn Gln Ala Gln Ala Arg Arg
                565                 570                 575

Lys

<210> SEQ ID NO 23
<211> LENGTH: 329
<212> TYPE: PRT
<213> ORGANISM: Human

<400> SEQUENCE: 23

Met Ala Thr Gly Gln Lys Leu Met Arg Ala Val Arg Val Phe Glu Phe
1               5                   10                  15

Gly Gly Pro Glu Val Leu Lys Leu Arg Ser Asp Ile Ala Val Pro Ile
                20                  25                  30

Pro Lys Asp His Gln Val Leu Ile Lys Val His Ala Cys Gly Val Asn
            35                  40                  45

Pro Val Glu Thr Tyr Ile Arg Ser Gly Thr Tyr Ser Arg Lys Pro Leu
        50                  55                  60

Leu Pro Tyr Thr Pro Gly Ser Asp Val Ala Gly Val Ile Glu Ala Val
65                  70                  75                  80

Gly Asp Asn Ala Ser Ala Phe Lys Gly Asp Arg Val Phe Thr Ser
                85                  90                  95

Ser Thr Ile Ser Gly Gly Tyr Ala Glu Tyr Ala Leu Ala Ala Asp His
            100                 105                 110

Thr Val Tyr Lys Leu Pro Glu Lys Leu Asp Phe Lys Gln Gly Ala Ala
        115                 120                 125

Ile Gly Ile Pro Tyr Phe Thr Ala Tyr Arg Ala Leu Ile His Ser Ala
    130                 135                 140

Cys Val Lys Ala Gly Glu Ser Val Leu Val His Gly Ala Ser Gly Gly
145                 150                 155                 160

-continued

```
Val Gly Leu Ala Ala Cys Gln Ile Ala Arg Ala Tyr Gly Leu Lys Ile
                165                 170                 175

Leu Gly Thr Ala Gly Thr Glu Glu Gly Gln Lys Ile Val Leu Gln Asn
            180                 185                 190

Gly Ala His Glu Val Phe Asn His Arg Glu Val Asn Tyr Ile Asp Lys
            195                 200                 205

Ile Lys Lys Tyr Val Gly Glu Lys Gly Ile Asp Ile Ile Glu Met
        210                 215                 220

Leu Ala Asn Val Asn Leu Ser Lys Asp Leu Ser Leu Leu Ser His Gly
225                 230                 235                 240

Gly Arg Val Ile Val Val Gly Ser Arg Gly Thr Ile Glu Ile Asn Pro
                245                 250                 255

Arg Asp Thr Met Ala Lys Glu Ser Ser Ile Ile Gly Val Thr Leu Phe
                260                 265                 270

Ser Ser Thr Lys Glu Glu Phe Gln Gln Tyr Ala Ala Ala Leu Gln Ala
            275                 280                 285

Gly Met Glu Ile Gly Trp Leu Lys Pro Val Ile Gly Ser Gln Tyr Pro
    290                 295                 300

Leu Glu Lys Val Ala Glu Ala His Glu Asn Ile Ile His Gly Ser Gly
305                 310                 315                 320

Ala Thr Gly Lys Met Ile Leu Leu Leu
                325

<210> SEQ ID NO 24
<211> LENGTH: 125
<212> TYPE: PRT
<213> ORGANISM: Human

<400> SEQUENCE: 24

Met Gln Pro Ala Ser Ala Lys Trp Tyr Asp Arg Arg Asp Tyr Val Phe
1                5                  10                  15

Ile Glu Phe Cys Val Glu Asp Ser Lys Asp Val Asn Val Asn Phe Glu
            20                  25                  30

Lys Ser Lys Leu Thr Phe Ser Cys Leu Gly Gly Ser Asp Asn Phe Lys
        35                  40                  45

His Leu Asn Glu Ile Asp Leu Phe His Cys Ile Asp Pro Asn Asp Ser
    50                  55                  60

Lys His Lys Arg Thr Asp Arg Ser Ile Leu Cys Cys Leu Arg Lys Gly
65                  70                  75                  80

Glu Ser Gly Gln Ser Trp Pro Arg Leu Thr Lys Glu Arg Ala Lys Leu
                85                  90                  95

Asn Trp Leu Ser Val Asp Phe Asn Asn Trp Lys Asp Trp Glu Asp Asp
            100                 105                 110

Ser Asp Glu Asp Met Ser Asn Phe Asp Arg Phe Ser Glu
        115                 120                 125
```

BIOMARKERS FOR LIVER DISEASES AND METHOD FOR USING THE SAME

CROSS REFERENCES TO THE RELATED APPLICATIONS

This is a continuation application of U.S. application Ser. No. 12/073,603 filed Mar. 7, 2008, now abandoned, which is a division of U.S. application Ser. No. 11/013,684 filed Dec. 17, 2004, now abandoned.

BACKGROUND OF THE INVENTION

1. Field of the Invention

The present invention is related to biomarkers for liver diseases and method for using the same, in which a method for screening autoantigens is employed to identify biomarkers that can be used in detecting liver diseases. The identified biomarkers are further developed into detection kits to detect the presence of autoantibodies or autoantigens in specimens for screening of liver diseases.

2. Description of Related Art

People with impaired immune functions are prone to develop immune diseases. The etiology of many human diseases may be traced to our immune system in any of the three conditions described below. The first is reduced immunity, lower activity of immune cells, or reduced quantity of immune cells, such that the human body cannot fight off the invading bacteria, virus or mold, and becomes susceptible to contagious diseases, such as common cold, flu, pneumonia, enteritis, or even hepatitis and AIDS. The second condition is immunodeficiency or over-reaction of the immune system where the invading substances are not germs, but tiny pollens or macromolecular proteins in the food ingested, against which the immune system releases a large amount of antibodies. Such attack and defense occur in our cells, causing a chain of reactions which is also called allergy. When real pathogens such as bacteria, virus or mold attack the human body at this time, the immune system is no longer able to put up resistance. The third condition of impaired immune system is the immune cells attack normal cells in the human body, called autoimmune disorder as in the case of rheumatoid arthritis, lupus erythematous, and herpes. Such immune diseases arise from our own immune system having an identification problem that autoantibodies are produced against human body's own cells, resulting in tissue damage and illnesses.

It is now known that autoantibodies are present not just in autoimmune diseases. More and more studies indicate that in the immune response to cancer, autoantigen (from the tumor) and autoantibody (from the body) exist in some cases. Thus the detection of tumor autoantigen that elicits body response may be directed towards and applied in the testing, diagnosis, or prognosis of cancer, and furthermore, in the treatment of disease.

U.S. Pat. No. 6,631,330, 5,137,807, 5,830,667, 6,264,949, and 5,985,542 disclose the use of biomarkers in the diagnosis of cirrhosis, fibrosis or autoimmune hepatitis (AII-I); U.S. Pat. Nos. 4,994,374 and 5,175,084 disclose the use of biomarkers in the diagnosis of hepatocellular carcinoma; U.S. Pat. No. 6,410,724 uses DNA primer associated with hepatocellular carcinoma as a diagnostic tool. But the biomarkers disclosed in those patents lack accuracy or are susceptible to interference to a certain extent.

U.S. Pat. No. 5,891,436 and Publication No. 20030138860 disclose the use of biomarkers to detect the presence of autoantibodies in human serum as a diagnostic tool for primary biliary cirrhosis or hepatocellular carcinoma. Those patents confirm the existence of autoantibodies in cancer patients and thereby establish the rational for using biomarkers in cancer screening.

Cancer has been the leading cause of death in Taiwan since 1982, whereas liver cancer is ranked among the top as the cause of death in both men or women. Thus it is important to find biomarkers with high accuracy and not susceptible to interference and use those biomarkers to develop detection kits for liver cirrhosis and cancer to effectively screen patients with liver diseases in the hope that early diagnosis and early treatment can help lower the mortality rate.

SUMMARY OF THE INVENTION in addressing the drawbacks of prior arts, the present invention provides biomarkers for liver diseases, which can be developed into detection kits for diagnosis of liver cirrhosis and liver cancer based on the knowledge of the existence of autoantibodies.

An objective of the present invention is to provide biomarkers for detecting liver cirrhosis and liver cancer, which are selected from any one of the amino acid sequences with SEQ ID NO:1 to SEQ ID NO:24 or derivatives or fragments or variants or the combination thereof or the antibodies against the amino acid sequences.

According to the present invention, the aforesaid variants are obtained by substituting, deleting, inserting and/or adding to the amino acid in the amino acid sequences of the biomarker with one or more amino acids; the amino acid sequence of the variant and that of the biomarker have sequence homology greater than 80%.

Another objective of the present invention is to provide a detection kit for liver diseases, comprising a set of biomarkers selected from any one of the amino acid sequences with SEQ ID NO:1 to SEQ ID NO:24 or derivatives or fragments or variants or the combination thereof.

In one embodiment of the present invention, the aforesaid detection kit may further include secondary antibodies that can recognize the antibodies against any one of the amino acid sequences with SEQ ID NO:1 to SEQ ID NO:24 or derivatives or fragments or variants thereof.

A further objective of the present invention is to provide a method for screening liver diseases, comprising the steps of: providing a specimen; using biomarkers selected from any one of the amino acid sequences with SEQ ID NO:1 to SEQ ID NO:24 or derivatives or fragments or variants or the combination thereof to capture the autoantibody in the specimen; and detecting the autoantibody.

Yet another objective of the present invention is to provide a detection kit for liver diseases, comprising a set of antibodies against any one of the amino acid sequences with SEQ ID NO:1 to SEQ ID NO:24.

A further objective of the present invention is to provide a method using the aforesaid detection kit to screen liver diseases, comprising the steps of: providing a specimen; using the antibody against any one of the amino acid sequences with SEQ ID NO:1 to SEQ ID NO:24 to capture the antigen in the specimen; and detecting the antibody-antigen complex.

This invention is based on the use of autoantigen screening method, comprising the steps of: firstly purifying antibodies from normal persons, liver cirrhosis patients, and liver cancer patients respectively and immobilizing them in different columns; passing the cell extracts from liver disease related cell lines (HepG2 C3A & SNU-387) in sequence through the normal antibody column and patient antibody column to obtain autoantigens associated with liver cirrhosis and liver cancer; using those autoantigens as biomarker kits coupled with enzyme-linked immunosorbent assay (ELISA), radioimmunoassay (RIA), or immunofluorescence to detect the presence of autoantibodies against said autoantigens in the screened specimen, and based on which, to determine whether the patient has liver cirrhosis or liver cancer. Since those biomarkers are identified based on existing autoantibodies, they can be developed into diagnostic kits to determine if the patient has such diseases based on the presence of autoantibodies against the biomarkers. Such method is much easier than direct screening of the antigen and offers greater accuracy and sensitivity.

DETAILED DESCRIPTION OF THE INVENTION

Figure 1:
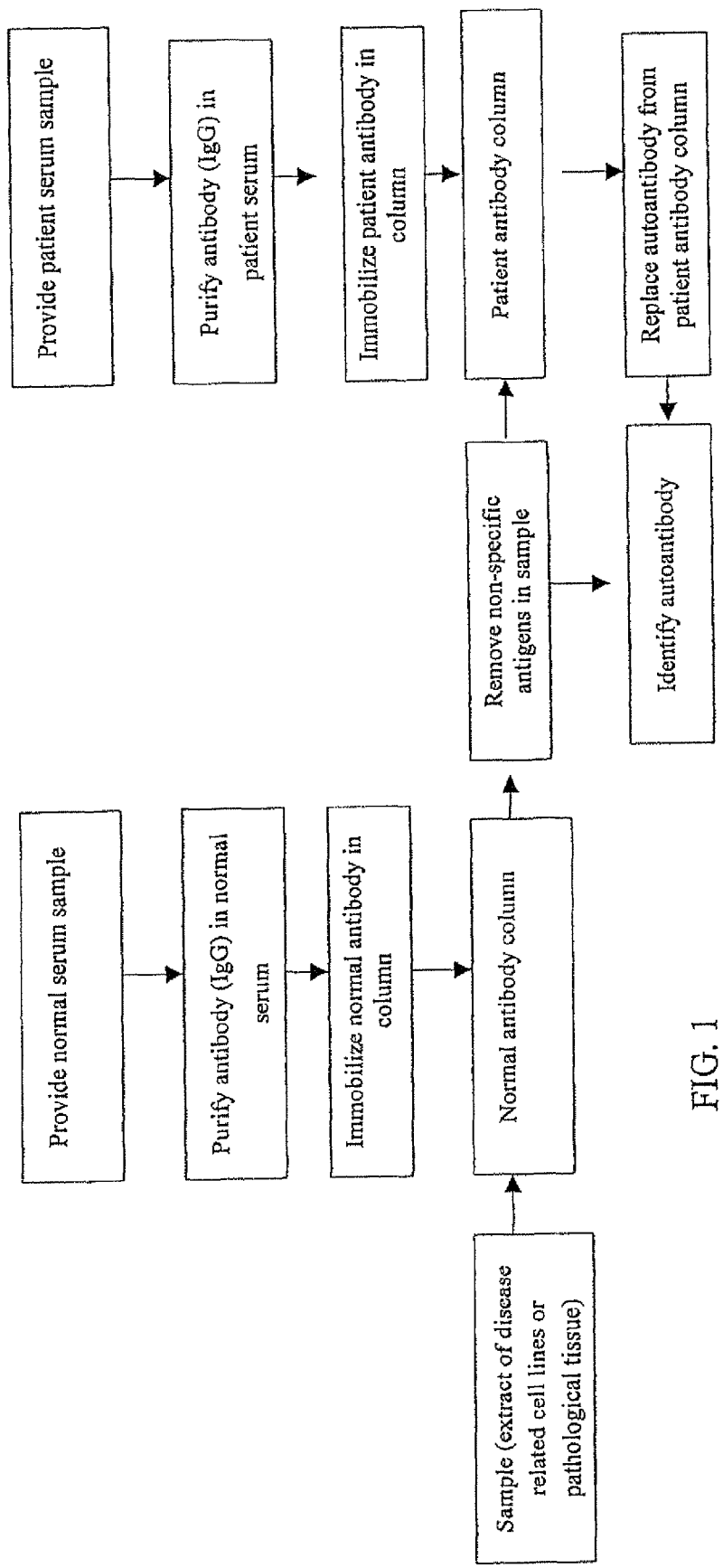
FIG. 1 shows a flow chart of an autoantigen screening method according to the present invention.

The present invention relates to the use of an autoantigen screening method to identify biomarkers that may be used in the detection of liver diseases, such as liver cirrhosis and liver cancer. Said autoantigen screening method as shown in FIG. 1 comprises the following steps: firstly obtaining serum samples from normal persons and patients and passing the respective samples over affinity columns that can capture antibodies to purify the antibodies contained in the serum samples; next packing respectively the resulting purified normal antibodies and patient antibodies into columns to obtain a column containing antibodies from normal persons (normal antibody column) and a column containing antibodies from patients (patient antibody column) in which antibodies are immobilized through the chemical bonding formed between the antibodies and chemical functional groups in the column; obtaining a sample which may be the extract of disease related cell lines or pathological tissues; the aforesaid serum sample may be that of a single patient or a mixture sample containing the sera of a plurality of patients.

To continue the procedure, passing the sample from the extract of disease related cell lines or pathological tissues over the normal antibody column where non-specific antigens are captured and retained in the column through the specific affinity of normal antibodies; this step may be viewed as pre-treatment of the sample before the patient antibody column is used to screen autoantigens in the sample. After non-specific antigens are removed, the sample constitutes only specific antigens. Next, passing the sample over the column packed with patient antibodies to screen disease related autoantigen. Since non-specific antigens have been removed by normal serum antibodies, the autoantigens as identified by patient's autoantibodies are more specific.

Finally, the autoantigens displaced from the patient antibody column are subjected to determination by the mass spectrum technology; the aforesaid determination procedure involves comparing the signals from mass spectrograph with the database to obtain the information on the autoantigens.

Autoantigens in liver disease related cell lines are purified and identified according to the method described above. Given that those autoantigens are identified by the antibodies in patient sera, the autoantigens or derivatives or fragments or variants or combinations thereof can be utilized as biomarkers and developed into detection kits. By detecting the presence of autoantibodies in screened specimen, it can be determined whether the patient has liver cirrhosis or other liver diseases. In addition to biomarkers, the detection kits can further include secondary antibodies that can recognize the autoantibodies against the biomarkers to facilitate the application of the detection method.

Figure 2:
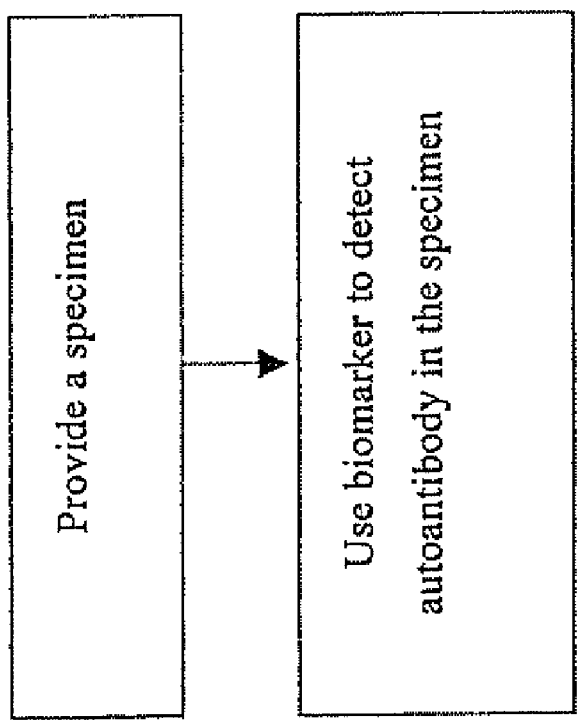
FIG. 2 shows a flow chart of using biomarkers for screening autoantibody according to the present invention.

As shown in FIG. 2, the screening method utilizing the detection kits described above comprises the steps of: providing a specimen; using biomarkers to capture the autoantibody in the specimen; and detecting the autoantibody. Said biomarkers are selected from autoantigens screened by the autoantigen screening method or its derivatives or fragments or variants or the combination thereof. The aforesaid specimen is whole blood or serum, preferably serum.

To facilitate the detection, the aforesaid biomarker may come in any form, including but not limited to, a detection kit or pre-immobilized on a substrate, said substrate may be an immunoassay plate or a biochip, said substrate may be an immunoassay plate or a biochip. The autoantibodies in the specimen captured by the biomarkers can be recognized and adsorbed by the secondary antibodies, which are modified antibodies having special functional groups for color reaction, radio detection or fluorescence detection.

After autoantibody is adsorbed by the secondary antibody, a special reagent is added to undergo color reaction and enzyme-linked immunosorbent assay (ELISA) is employed to determine the presence of the secondary antibody, and from which to learn the presence of the autoantibody as a basis for determining if the patient has liver cancer or liver cirrhosis. The presence of the secondary antibody and thereby the presence of the autoantibody can also be determined by radioimmunoassay (RIA) or immunofluorescence.

If the screening method does not include the secondary antibody, the specimen may be labeled with a fluorescence marker (e.g. cy3 or Cy5) prior to reacting with the biomarkers. The fluorescence-labeled autoantibodies screened by the biomarkers can then be detected by a fluorescence scanner without the use of the secondary antibody.

Besides detecting the presence of the autoantibody, detection of the antigen may also be used as a basis for determining whether a patient has liver cirrhosis or liver cancer. To achieve this purpose, the present invention also provides a detection kit containing antibodies that can recognize autoantigens identified by the autoantigen screening method for the screening of liver diseases.

The method of using the aforesaid detection kit for screening liver cancer and liver cirrhosis comprises the steps of: providing a serum specimen; using the aforesaid antibody to recognize and capture the antigen in the serum; and detecting the antibody-antigen complex.

The advantages of the present invention are further depicted with the illustration of an example, but the descriptions made in the example should not be construed as a limitation on the actual application of the present invention.

EXAMPLE 1

Screening of Autoantigens Using Autoantibodies in Sera of Patients With Liver Diseases Purification of Autoantibodies in the Serum Sample Firstly obtaining a serum of a patient with liver cirrhosis or liver cancer, diluting the serum with a binding buffer (20 mM PBS, pH 7.0) at the ratio of 1:10, and then filtering the diluted serum using a 0.45 µm filter membrane to prevent the blockage of column in subsequent steps; next rinsing a Protein G affinity column with the binding buffer ten times the column volume at the rate of 1 ml/min, and then passing the filtered serum sample over the Protein G affinity column at the rate of 0.2 ml/min to retain the antibodies in the column through affinity; rinsing the Protein G affinity column again using the binding buffer 5-10 times the column volume at the rate of 1 ml/min to remove substances in the serum sample that do not form affinity bonding with the column. Eluting antibodies from the column using an elution buffer (0.1 M Glycine-HCl, pH 2.7) 2-5 times the column volume at the rate of 1 ml/min and collecting the elated antibodies in a test tube which is added beforehand with 60-200 µl Tris-HCL solution (1M, pH 9.0). Finally displacing the sample in a coupling buffer (0.2M $NaHCO_3$, 0.5M NaCl, pH 8.3) to complete the purification of autoantibodies (IgG) in the serum sample.

The method according to the present invention requires one normal IgG and patient IgG column each. Thus sera from normal persons and patients should be obtained and subject to the purification steps described above.

Preparation of Columns Containing Autoantibodies

Pipette one drop of an acidification solution (1 mM HCl, ice bathed) into a NHS-activated column to prevent the formation of bubbles. After connecting the upper end of the column with a syringe or pump, removing the adapter at the-bottom of the column. Rinsing out isopropanol in the column using the acidification solution two times the column volume. After repeating the wash step three times, injecting the sample containing autoantibodies into the column. Preparing the aforesaid coupling buffer containing purified autoantibodies into a solution with a volume equivalent to one time the column volume and a concentration of 0.5-10 mg/ml. After passing the aforesaid sample containing autoantibodies over the column, sealing the column and let the reaction go on for 15-30 minutes under 25° C. or 4 hours under 4° C. to immobilize the antibodies in the column through chemical bonding.

After the bonding between the autoantibodies and the column, eluting the column with a blocking buffer (0.5M ethanolamine, 0.5M NaCl, pH 8.3) two times the column volume, and repeating the steps three times. Then rinsing the column with a washing buffer (0.1M acetate, 0.5M NaCl, pH 4) two times the column volume and also repeating the steps three times. Again eluting the column three times using the aforesaid blocking buffer two times the column volume each time, and then let the column react 15-30 minutes to block and inactivate the functional groups in the column that are not bound with autoantibodies. After completing the blocking reaction, rinsing the column three times using the aforesaid washing buffer two times the column volume each time, followed by eluting the column three times using the aforesaid blocking buffer two times the column volume to make sure all functional groups not bound with autoantibodies are blocked. Again rinsing three times the column using the washing buffer two times the column volume each time. Finally eluting the column with a pH neutral buffer 2-5 times the column volume to complete the preparation of the column packed with the autoantibodies.

Identification of Autoantigens from Extract of Liver Disease Related Cell Lines

Firstly rinsing 2.68 mg of HepG2 C3A cells with culture medium removed with an ice-bathed Iris saline solution (50 mM Tris pH 7.5, 150 mM NaCl, 1.5 mM PMSF, phosphatase inhibitors) twice, then adding in 1 ml of Triton Extraction solution (15 mM Tris pH 7.5, 120 mM NaCl, 25 mM KCl, 2 mM EGTA, 0.1 mM DTT, 0.5% Triton X-100, 10 µg/ml leupeptin, 0.5 mM PMSF, and phosphatase inhibitors) and let it stand for 30 minutes under 4° C. At this time, cells start to decompose and release proteins. Centrifuging (with a table-top centrifuge) the solution at 14,000 rpm under 4° C. for 15 minutes to remove solid, insoluble cell structures. Collecting the supernatants to carry on immunoaffinity chromatography.

After diluting the cell extract collected with the binding buffer at the ratio of 1:10, passing it through a 0.45µ filter membrane to prevent the blockage of the column in subsequent steps. Prior to injecting the sample into the IgG column, rinsing the normal and patient antibody columns with the binding buffer ten times the column volume at the rate of 1 ml/min. Then passing the filtered cell extract over the normal antibody column at the rate of 0.2 ml/min. Eluting the normal antibody column with the binding buffer 5-10 times the column volume at the rate of 1 ml/min. At this time, antigens in the cell extract that are identified and captured by the normal antibodies will be retained in the column. The purpose of this step is to remove non-specific antigens in the HepG2 C3A cells. As a result, the cell extract that has passed through the column is free of non-specific antigens. Injecting the resulting cell extract into the patient antibody column. Eluting the column with the binding buffer 5-10 times the column volume at the rate of 1 ml/min. At this time, the autoantigens present in the cell extract will be captured by the autoantibodies from the patients and retained in the column. When the cell extract passes over the normal antibody column, the antigens captured by the normal antibodies are retained in the column, whereas the cell extract free of antigens can be identified and captured by the normal antibodies, only antigens that can be identified and captured by the patient antibodies will be retained by the column. The antigens retained in the patient antibody column are eluted and collected using the elution buffer 2-5 times the column volume at the rate of 1 ml/minl. Subjecting the flow-through to protein hydrolysis using trypsin and the resulting peptides are assayed using the mass spectrum technology. The resulting spectrographs are compared with the database to obtain the information on the proteins.

By screening liver disease related cell lines with autoantibodies in the serum of the patients with liver cirrhosis or liver cancer, the following autoantigens are obtained:

1. Nucleoside diphosphate kinase (gi|1421609, SEQ ID NO.1).
2. NM23 protein (gi|35068, SEQ ID NO.2).
3. ATP synthase beta chain, mitochondrial [precursor] (gi|28940, SEQ ID NO.3).
4. 14-3-3 zeta protein (tyrosine 3/tryptophan 5-monooxygenase activation protein) (gi|4507953, SEQ ID NO.4).
5. 14-3-3 epsilon protein (tyrosine 3/tryptophan 5-monooxygenase activation protein) (gi|4507953, SEQ ID NO.5).
6. Protein disulfide isomerase-related protein 5 (gi|1710248, SEQ ID NO.6).
7. Unnamed protein product (gi|21750187, SEQ ID NO.7).
8. Tropomyosin alpha 3 (gi|37403, SEQ ID NO.8).
9. Trypomyosin alpha 4 (gi|10435300, SEQ ID NO.9).
10. Calreticulin precursor (gi|4757900, SEQ ID NO.10).
11. Human pre-mRNA splicing factor SF2p32 (gi|338043, SEQ ID NO.11).
12. Tumor necrosis factor type I receptor associated protein TRAP-1 (gi|1082886, SEQ ID NO.12).
13. Tumor rejection antigen (gp96) 1; glucose regulated protein (gi|4507677, SEQ ID NO.13).
14. Heat shock protein 90-beta (gi|72222, SEQ ID NO.14).
15. Heat shock protein 90-alpha (gi|23678, SEQ ID NO.15).
16. Heat shock 60kDa protein 1 (gi|31542947, SEQ ID NO.16).
17. HMG-1 (gi|968888, SEQ ID NO.17).
18. KIAA0144 gene product (NICE-4 protein) (gi|13111995, SEQ ID NO.18).
19. Valosin-containing protein (p97); transitional endoplasmic reticulum ATPase (gi|6005942, SEQ ID NO.19).
20. Glyceraldehyde 3-phosphate dehydrogenase, liver (gi|30157565, SEQ ID NO.20).
21. Cytokeratin (gi|1419564, SEQ ID NO.21).
22. IGF-II mRNA-binding protein 1 (gi|4191608, SEQ ID NO.22).
23. NADPH: quinone reductase (gi|13236495, SEQ ID NO.23).
24. Crystal Structure of The Human Co-Chaperone P23 (hsp-90 co-chaperone) (gi|9257073, SEQ ID NO.24).

The autoantigens identified with the antibodies from liver disease related cell lines are shown in Table 1; the left side of the Table 1 lists the GI number and name of the proteins and the right side indicates the autoantigens that may be identified from cell lines using sera of patients with liver cirrhosis or liver cancer. As shown, those autoantigens are not just present in one liver disease, they are repeatedly identified in different cell lines using autoantibodies in sera of different sources, indicating their close correlation with liver diseases. Some proteins listed in Table 1 have two GI numbers. That is because the protein and its variant had similar results in the mass spectrometry.

Gelatin, 0.15M NaCl, 5 mM EDTA•2Na, 0.05% Tween-20, 50 mM Tris base, or b. 1% BSA-PBS, pH=7.4, or c. 5% non-fat milk-PBS, pH=7.4) and let blocking reaction go on for at least 2 hours under ambient temperature; after the reaction is completed, washing with a PBST buffer three times and then depositing a 100 μl/well serum solution to be

TABLE 2

Autoantigens screened from liver disease related cell lines

| GI number | Name of protein | Liver cirrhosis serum vs. HepG2 C3A | Liver cancer serum vs. HepG2 C3A | Liver cirrhosis serum vs. SNU-387 | Liver cancer serum vs. SNU-387 |
|---|---|---|---|---|---|
| 1421609 | Nucleoside Diphosphate Kinase (=NM23 protein) | ● | ● | ● | ● |
| 28940 | ATP synthase beta chain, mitochondrial [Precursor] | ● | ● | ● |  |
| 4507953, 5803225 | 14-3-3 protein | ● |  | ● |  |
| 1710248 | Protein disulfide isomerase-related protein 5 |  | ● |  | ● |
| 21750187 | Gi|21750187 Unnamed protein product (RAN_rec_mot.) |  | ● |  |  |
| 37403, 10435300 | Tropomyosin |  |  | ● | ● |
| 4757900 | Calreticulin precursor | ● | ● |  |  |
| 338043 | Human pre-mRNA splicing factor SF2p32, complete sequence | ● | ● |  |  |
| 1082886 | Tumor necrosis factor type 1 receptor associated protein TRAP-1 | ● | ● |  |  |
| 4507677 | Tumor protein antigen (gp96)1; glucose regulated protein | ● | ● |  |  |
| 72222, 123678 | Heat shock protein 90 | ● | ● |  |  |
| 31542947 | Heat shock 60 kDa protein 1 (chaperonin); mitochondrial matrix protein P1 | ● |  |  |  |
| 968888 | HMG-1 (high-mobility group-1) | ● |  |  |  |
| 13111995 | KIAA0144 gene product (NICE-4 protein) | ● |  |  |  |
| 6005942 | Valosin-containing protein (p97); transitional endoplasmic reticulum ATPase | ● |  |  |  |
| 30157565 | Glyceraldehyde 3-phosphate dehydrogenase, liver | ● |  |  |  |
| 1419564 | Cytokeratin | ● |  |  |  |
| 4191608 | IGF-II mRNA-binding protein 1 | ● |  |  |  |
| 13236495 | NADPH-quinone reductase |  |  | ● |  |
| 9257073 | Crystal Structure of The Human Co-Chaperone P23 (hsp-90 co-chaperone) |  |  | ● |  |

EXAMPLE 2

Determining the Availability of Autoantigens Identified by the Autoantigen Screening Method To demonstrate the availability of 24 autoantigens identified in Example 1, further assay of serum samples from normal persons, liver cirrhosis patients and liver cancer patients using immunoassay (ELISA, RIA or immunofluorescence) and the aforesaid 24 biomarkers is carried out. The assay method includes the following steps as shown in FIG. 2: providing a specimen; using the biomarker selected from any one of the amino acid sequences with SEQ ID NO:1 to SEQ ID NO:24 or derivatives or fragments or variants or the combination thereof to capture the autoantibody in the specimen; and detecting the autoantibody.

In the example of enzyme-linked immunosorbent assay (ELISA), the following steps are taken: firstly diluting the biomarker with a coating buffer (choice of a. 50 mM $Na_2HCO_3$, pH=9.6, or b. 20 mM Tris-HCl, pH=8.5, or c. 10 mM PBS, pH=7.4) to a concentration of 0.5~10 μg/ml, where the coating buffer is selected according to the PI value of the biomarker, preferably a buffer having pH 1~2 higher than pi. Adding 100 μl/well biomarker solution to ELISA plate and let it stand overnight under 4° C. for immobilization.

To continue the procedure, removing an unattached biomarker by washing the plate with a PBST buffer twice (PBST buffer: PSB buffer+0.05% Tween-20), then adding a 200 μl/well blocking buffer (choice of a. Gelatin-NET: 0.5% assayed (a serum solution is obtained by diluting the serum sample 1000 times with the blocking buffer). At this time, the autoantibodies in the serum will react with immobilized biomarkers. After reaction for at least 2 hours under ambient temperature, washing the plate four times with the PBST buffer and then adding in a 1000 μl/well secondary antibody (diluted 5000 times with the blocking buffer). At this time, the secondary antibody would recognize and adsorb the autoantibody. After reaction for at least 1 hour under ambient temperature, washing the plate five times with the PBST buffer. Then adding in a 100 μl/well TMB to elicit color reaction for 30 minutes. Afterwards, adding a 100 μl/well 0.5M $H_2SO_4$ and detecting absorbance at 450 nm.

To make sure the expression of the autoantibody can be used for diagnosis of liver cirrhosis and/or liver cancer, ELISA is employed to obtain the absorbance values of autoantibodies in the sera of normal persons, liver cirrhosis patients and liver cancer patients as identified by respective autoantigens. The data derived from five proteins-GADPH, NADPH, HMG-1, NM23 and Cytokeratin are subject to biostatistical analysis and Wilcoxon-Mann-Whitney Test. The following results at a 95% confidence level as shown in the table below are obtained:

|  | GADPH | NADPH | HMG-1 | NM23 | Cytokeratin |
| --- | --- | --- | --- | --- | --- |
| Normal person vs. Liver cirrhosis patient | p = 0.001 | p = 0.001 | p = 0.00006 | p = 0.0001 | p = 0.001 |
| Normal person vs. Liver cancer patient | p = 0.017 | p = 0.016 | p = 0.015 | p = 0.002 | p = 0.016 |
| Liver cirrhosis patient vs. Liver cancer patient | p > 0.05 | p > 0.05 | p > 0.05 | p > 0.05 | p > 0.05 |

Normal person: N = 10; liver cirrhosis patient: N = 15; liver cancer patient: N = 21 (the assumption of p < 0.05 is valid)

Assuming there are differences between the expressions of biomarker-detected autoantibodies in normal persons, liver cirrhosis patients and liver cancer patients, the table above shows that such assumption was valid in normal persons versus liver cirrhosis patients and normal persons versus liver cancer patients, meaning the differences in the expression levels of biomarker-detected autoantibodies between normal persons and liver cirrhosis patients and between normal persons and liver cancer patients are statistically significant.

Statistics shows that the expression levels of GADPH-detected autoantibodies in normal persons and liver cirrhosis patients differed by 8.375 folds, while that in normal persons and liver cancer patients differed by 4.86 folds; the expression levels of HMG-1—detected autoantibodies in normal persons and liver cirrhosis patients differed by 74 folds; the expression levels of NM23-detected autoantibodies in normal persons and liver cirrhosis patients differed by 24 folds, while that in normal persons and liver cancer patients differed by 8.545 folds. These results demonstrate that the expression levels of the antibodies in liver cirrhosis and liver cancer patients as detected by the 24 autoantigens provided herein were higher than those in normal persons. Thus a detection kit using those 24 autoantigens coupled with immunoassay may be applied in the screening of liver cirrhosis and liver cancer based on the expression levels of autoantibodies in the screened specimens.

The preferred embodiment of the present invention as disclosed above is not meant to limit this invention. All modifications and alterations made by those familiar with the skill without departing from the spirits of the invention and appended claims shall remain within the protected scope and claims of the invention.

What is claimed is:

1. A method of detecting liver cirrhosis or liver cancer in a subject, comprising the steps of:
    (a) providing a specimen of serum from a subject suspected of having liver cirrhosis or liver cancer;
    (b) using a biomarker consisting of SEQ ID NO:23 to identify and capture autoantibodies in the specimen by contacting the biomarker with the specimen to form a biomarker-autoantibody complex;
    (c) detecting the biomarker-autoantibody complex in step (b): and
    (d) correlating the presence of the biomarker-autoantibody complex with liver cirrhosis or liver cancer, wherein the presence of the biomarker-autoantibody complex indicates that the subject has liver cirrhosis or liver cancer.

2. The method according to claim 1, wherein said biomarker is made into detection kits.

3. The method according to claim 1, wherein said biomarker is firstly immobilized on a substrate.

4. The method according to claim 3, wherein said substrate is an immunoassay plate or a biochip.

5. The method according to claim 1, wherein the method further includes a step of using a secondary antibody to recognize and adsorb the autoantibody.

6. The method according to claim 5, wherein said secondary antibody is modified and has a special functional group detectable by means of color reaction, radioactivity or fluorescence.

7. The method according to claim 1, wherein the detection of the autoantibody is achieved by using a fluorescence scanner to detect a fluorescence-labeled autoantibody.

8. The method according to claim 1, wherein the detection of the autoantibody is achieved by detection of the secondary autoantibody with enzyme—linked immunosorbent assay (ELISA), radioimmunoassay (RIA) or immunofluorescence.

* * * * *